(12) United States Patent
Claessens et al.

(10) Patent No.: US 10,588,506 B2
(45) Date of Patent: Mar. 17, 2020

(54) DEVICE AND METHOD FOR THE QUANTITATIVE DETECTION OF DISORDERS IN THE FIELD OF VISION

(71) Applicants: Daniela Claessens, Düsseldorf (DE); Ronald V. Krüger, Düsseldorf (DE)

(72) Inventors: Daniela Claessens, Düsseldorf (DE); Ronald V. Krüger, Düsseldorf (DE)

(*) Notice: Subject to any disclaimer, the term of this patent is extended or adjusted under 35 U.S.C. 154(b) by 47 days.

(21) Appl. No.: 15/752,735

(22) PCT Filed: Aug. 11, 2016

(86) PCT No.: PCT/EP2016/069156
§ 371 (c)(1),
(2) Date: Feb. 14, 2018

(87) PCT Pub. No.: WO2017/029193
PCT Pub. Date: Feb. 23, 2017

(65) Prior Publication Data
US 2018/0235459 A1 Aug. 23, 2018

(30) Foreign Application Priority Data
Aug. 14, 2015 (DE) .......................... 10 2015 215 557

(51) Int. Cl.
*A61B 3/032* (2006.01)
*A61B 3/024* (2006.01)
(Continued)

(52) U.S. Cl.
CPC ............. *A61B 3/032* (2013.01); *A61B 3/024* (2013.01); *G06F 3/013* (2013.01); *G06F 17/11* (2013.01)

(58) Field of Classification Search
CPC ..... A61B 3/032; A61B 3/0025; A61B 3/0041; A61B 3/0033; A61B 3/036
(Continued)

(56) References Cited

U.S. PATENT DOCUMENTS 3,668,743 A 6/1972 Roberts
5,589,697 A * 12/1996 Smayling .............. H01L 27/115
257/204
(Continued)

FOREIGN PATENT DOCUMENTS

| CN | 203576469 | 5/2014 |
|----|-----------|--------|
| GB | 2457735 | 2/2008 |
| WO | 2010023470 | 8/2009 |

*Primary Examiner* — Mohammed A Hasan
(74) *Attorney, Agent, or Firm* — Lewis Kohn & Walker LLP; David M. Kohn; Kari Moyer-Henry

(57) ABSTRACT

The present invention relates to a device and to a method for the quantitative detection of disorders in the field of vision of an eye of a test subject, in particular in the case of eye diseases which are associated with macular edema, wherein a square grid is displayed on a display device whose grid lines which are perceived by the test subject as curved can be modified by the subject in such a way that the subject can view an orthogonal reticule again. Such lines perceived as curved can be modified by input signals which modify the boundary curves defined by the boundary functions in such a way that the originally displayed linear reticule is perceived again, wherein the geometric deviations caused by transformation of the regions of the square reticule perceived as curved from the originally present squares are determined quantitatively as the sum of the absolute values of the horizontal deviations and as the sum of the absolute values of the vertical deviations.

23 Claims, 8 Drawing Sheets

(51) Int. Cl.
*G06F 3/01* (2006.01)
*G06F 17/11* (2006.01)

(58) Field of Classification Search
USPC .......................................................... 351/239
See application file for complete search history.

(56) References Cited

U.S. PATENT DOCUMENTS

| | | |
|---|---|---|
| 5,589,897 A | 12/1996 | Sinclair et al. |
| 5,892,570 A | 4/1999 | Stevens |
| 2005/0119739 A1* | 6/2005 | Glazier ................ A61F 2/1613 623/6.13 |
| 2007/0146631 A1 | 6/2007 | Sinclair et al. |
| 2007/0200927 A1 | 8/2007 | Krenik |
| 2010/0292999 A1 | 11/2010 | Verma |
| 2013/0194547 A1 | 8/2013 | Gierhart et al. |
| 2016/0089272 A1* | 3/2016 | Li ........................... A61H 5/00 128/845 |

\* cited by examiner

DEVICE AND METHOD FOR THE QUANTITATIVE DETECTION OF DISORDERS IN THE FIELD OF VISION

This application is a United States National Stage Application claiming the benefit of priority under 35 U.S.C. 371 from International Patent Application No. PCT/EP2016/069156 filed Aug. 11, 2016, which claims the benefit of priority from German Patent Application Serial No. DE 10 2015 215 557.9 filed Aug. 14, 2015, the entire contents of which are herein incorporated by reference.

DESCRIPTION

The present invention relates to a device for quantitatively detecting and/or monitoring disorders of the visual field of an eye of a subject according to the preamble of claim 1, and a method for quantitatively detecting disorders of the visual field of an eye of a subject where a metamorphopsia index ($M_g$) is calculated.

The present invention relates to quantitatively detecting, measuring and indicating disorders of the visual field of a human eye, in particular distortions (metamorphopsia [1]) and visual field deficits (scotoma).

Type of Disease

Various diseases of the eye can lead to accumulations of liquid in the center of the retina (macular edema), to the formation of a membrane on the retina (macular pucker), to the formation of a hole in the central retina (macula (layer) hole), or to the detachment of retinal layers (e.g., retinal pigment epithelial detachment). These kinds of medical conditions typically lead to disorders in the field of vision, such as distortions and scotomas.

Eye diseases leading to macular edema and thus to massive visual impairments up to blindness are, for example, age-related macular degeneration (AMD), diabetic macular edema, edema following retinal vein thrombosis, macular degeneration due to myopia, macular edema following cataract surgery, and inflammatory diseases (uveitis, central serous retinopathy).

Indications of AMD may symptomatically appear when the patient suddenly perceives straight lines as crooked or letters become blurred while reading.

AMD is an eye disease that leads to loss of vision in the area of the greatest acuity of vision, the so-called macula lutea (also called "yellow spot"). Daily activities, such as reading, watching TV, working at the monitor, driving, recognizing colors or recognizing faces become increasingly harder with progressing disease. Only the external visual field—and thus the patients' ability to orient themselves—is maintained. The risk of developing AMD increases steadily with age. Therefore, the current recommendation is that, from the age of 50, people should be examined annually by an ophthalmologist so that impending AMD can be recognized early.

There is a "dry" and a "wet" form of AMD. With around 85 percent, dry AMD is far more common. In this form, light-sensitive cells in the retina of the eye are lost over the years and thus vision is slowly lost, usually with the reading ability being preserved for a long time. Effective treatment options are so far not known, and intensive research focuses on the development of a substance intended to stop the progression of a special form of dry AMD (geographic atrophy), however, according to information from the manufacturer, a market launch is not expected until 2017 [2] (http://www.roche.com/investors/updates/inv-update-2014-09-15.htm). In the rarer but much more aggressive wet form of macular degeneration, abnormal blood vessels grow into the retina. The vessel walls break, bleed, leak fluid and lead to formation of edema below or in the retina.

Progressive scarring with destruction of the sensitive nerve layer in the retina results. In this progressive form, a massive loss of vision can occur within a short time. Age-related macular degeneration does not cause any pain. However, the first sign may be distorted vision: Straight lines appear crooked or wavy, contours are distorted, and colors become weaker. Soon vision losses occur in the form of spots that expand and can take up almost the entire field of vision, except for an outer circle.

Diagnostics

The precise ophthalmologic diagnosis of macular edema, such as is the case e.g., with AMD, is made using elaborate methods and techniques by specialists in ophthalmology, usually available only in specialized centers and hospitals. Thus, diagnosing macular edema includes Retinal examination: examination of the retina using a magnifying glass after administration of dilating eye drops Fluorescence angiography: fluorescence or indocyanine green angiography following injection of fluorescein or indocyanine green in an i.v. bolus and Optical coherence tomography (OCT).

Treatment of Macular Edema

Treatment of macular edema, for example, in cases with chronic "wet AMD" consists of repeated surgical procedures performed under sterile conditions in the operating room. Monthly intraocular injections of vascular epithelial growth factor VEGF antagonists are given by an ophthalmologist; on average 8 injections are needed each year.

Epidemiology

AMD is responsible for approximately 30 percent of all new cases of blindness worldwide and accounts for 50% of all new cases of blindness in Germany [3](http://cms.augeninfo.de/fileadmin/PDF/0512aa_267.pdf); it is therefore the most common cause of blindness in the western industrialized nations. In Germany, 4.5 million people suffer from macular degeneration; of these, 0.7 million suffer from the wet form that approximately 50,000 people are newly diagnosed with each year [4]. The prevalence of AMD increases with age: 14% of 55 to 64-year-olds are affected, and 37% of 75-year-olds and above.

Rapidly progressive wet AMD is the leading cause of blindness above the age of 60 in industrialized countries [5] (Bertram B: Blindness and visual impairment in Germany. Causes and incidence [Blindheit und Sehbehinderung in Deutschland: Ursachen und Häufigkeit]. The Ophthalmologist [Der Augenarzt], Volume 39, December 2005). Often, the disease is first noticed when the other eye is already affected as well. As one in four of 65-year-olds and above and one in three of 75-year-olds and above are already affected with various stages of AMD, early detection and—to the extent possible—prevention is particularly important. This is where the present invention comes into play.

Status of Health Care in Germany

The diagnosis and treatment of macular edema requires the consultation with a specialized center or a clinic and the use of economic resources. According to guidelines [6] and opinions [7] by professional societies (www.augeninfo.de), optical coherence tomography should be performed both prior to injection therapy and every month after the completed therapy cycle in the first half year. However, several public health insurance companies do not reimburse OCT examination. The patient is billed privately for this test: the cost of each examination is approximately EUR 100, and the purchase price for a spectral domain OCT that meets the requirements of the recommendations by the ophthalmological societies is approximately EUR 100,000.

Economic Significance

The prominent position of these ophthalmologically relevant diseases associated with macular edema results from the fact that 30 million people globally are currently suffering from AMD [8] (Rosenfeld P J, Martidis A, Tennant M T S: Age related macular degeneration Ophthalmology, 3rd edn Yanoff M, Duker J S Philadelphia: Mosby/Elsevier; 2009: 658-673) and that by 2030 this number is expected to double, due to demographic developments [4] (Finger R P, Fimmers R, Holz F G et al. Incidence of blindness and severe visual impairment in Germany: Projections for 2030. Invest Ophthalmol. Vis. Sci 2011; 52:4381-9). Thus, the present invention relates to a central problem of public health in an aging society.

From the perspective of economics, business, and public health, the following should be noted:

On the "World Sight Day" (Oct. 9, 2014), the European Forum Against Blindness (EFAB) announced the results of a study [9] conducted by the company Deloitte that included eleven countries (an expansion of the data reported last year from six countries) and addressed the economic impact of blindness and four major eye diseases. The study concluded that blindness and vision loss decrease the quality of life and increase the economic burden on society (http://www.e-fabeu.org/analytics). The study concluded that in the eleven countries studied, eye diseases could cause significant economic damages each year. Direct medical costs (costs of treatment, use of resources, provision of aids and magnifying vision aids) and indirect costs (costs of secondary complications, such as falls, lost workdays of victims or relatives) must hereby be taken into account.

The study, which included Denmark, France, Germany, Ireland, Italy, Poland, Slovakia, Spain, Sweden, Switzerland and the United Kingdom, reported that in these eleven countries:

1. 862,067 people are blind
2. 29,184,875 people are affected by severe vision impairment, namely by cataracts
3. 3,637,458 cases of diabetic retinopathy occur
4. 4,466,224 glaucoma patients exist; and
5. 2,013,228 people suffer from age-related wet macular degeneration (see: http://www.efabeu.org/analytics)

Blindness and the mentioned four eye diseases lead to a significant worsening of well-being. According to the aforementioned study, businesses lose 123 million working days each year. It is estimated that blindness and the eye diseases mentioned create economic costs of approximately 8 to 24 billion euros each year in the countries studied.

BACKGROUND OF THE INVENTION

Metamorphopsia is the most noticeable symptom of macular edema, e.g., in cases with macular degeneration, and scotoma is the main symptom of diseases such as wet or dry AMD and glaucoma.

In the clinical practice, the so-called Amsler Grid [10] has been a tried and trusted approach since approximately 1958 for qualitative detection of distortions and visual field loss (see Marc Amsler: The study of qualitative vision with the square grid. Instructions on the use of test panels [Die Untersuchung des qualitativen Sehens mit dem quadratischen Netz. Anweisungen zum Gebrauch der Testtafeln] Theodore Hamblin LTD, London 1958).

Although the Amsler grid can make only qualitative statements—due to test conditions—on perceived distortions and visual field losses, and cannot provide documentation or follow-up, even today it plays a significant role as a rapid screening method for the approximate determination of central visual field defects, for example, in cases with age-related macular degeneration or other exudative or degenerative processes in the central retina. It does not allow making substantial and detailed assessments of the visual field, for example, in terms of the quantitative degree of distortion. The test itself consists of an approximately 40 cm×40 cm square grid with a dot in the middle that the gaze must focus on during the monocular test. The other eye is completely covered with the palm of the hand or an eye patch, which is necessary for neurological reasons, since the brain is able to compensate small distortions of the visual impression of one eye by the "correct" visual impression of the other eye, and the subject will generally not detect distortions with binocular vision.

The test distance for the Amsler grid is approximately 40-50 cm. With corresponding findings, the subject will notice waves or curves in the grid, or also apparent "holes" in the grid or "dark spots" in the grid pattern. If experienced in a self-test, these types of perceptions should always lead to an immediate examination by the ophthalmologist.

Moreover, WO 2014/022850 A1 discloses methods for testing metamorphopsias using portable devices where a patient makes an entry into a displayed grid if he perceives a distortion. If he does, the program calculates the remaining area and divides it into additional segments. Then the process is repeated with each newly generated segment. If the segment appears distorted, it remains in the area to be tested, and if it does not, it is eliminated from further testing. The steps are repeated until the affected field of vision is isolated and can be represented as an area.

WO 2010/023470 A1 and US 2003/008176 A1 generally describe qualitative methods for detecting different visual disturbances.

Document GB 2457735 A relates to a method and a system for measuring visual field disturbances by deforming an (Amsler) grid pattern on the screen of a personal computer, where a patient with an impaired visual field perception can move the intersection points of the grid—for example by means of a computer mouse—in such a way that the grid is restored to its original state. Thus, the teaching of GB 2457735 A requires that the subject can see the intersecting points.

According to GB 2457735, a distortion can only be displayed in approximation: distortions located between only 2 adjacent nodes cannot be displayed.

The deviation of a straight line shown in FIG. 2 of GB 2457735 A represents only an approximation of the visual impression; therefore, the objectification the distorted perception GB 2457735 A is based on can be only an approximation. This is also evident from FIG. 4 of GB 2 57735 A, as wavy or curved distortions are not shown there either, which would be analogous to the visual impression of the diseased eye, but only tangents.

According to the teaching of GB 2457735 A, distortions perceived by the patient are evaluated equally regardless of location, and information on performing calculations is also not provided.

In GB 2457735 A, merely a sum index is calculated from a "magnitude" that is not further defined.

Moreover, according to GB 2457735 A, the distance between the eye and the screen is not controlled, making a quantitative standardized follow-up check impossible and an inter-individual comparison possible only on a qualitative basis.

Defects in the field of vision cannot be marked according to the teaching of GB 2457735 A.

In addition, the method disclosed by GB 2457735 A does not include a focus control. Therefore, changes in focus may lead to duplicate marking of distortions and thus to false recording of distortions (a newly performed focus leads to the entering the "same" distortion somewhere else.)

Moreover, U.S. Pat. No. 8,708,495 B2 discloses a method and an apparatus for correcting vision disorders as they occur in patients with macular degeneration. In particular, a quantitative diagnostic method is disclosed which is used to correct the visual field distortions of patients suffering from age-related macular degeneration. A computer-supported Amsler grid is generated which the patient perceives as distorted. The patient can then move individual intersection points of the grid so that he perceives the original undistorted Amsler grid. Then the computer system software computes two-dimensional displacement vectors from the adjustments the patient made for the individual intersection points and stores the derived vector field in the computer memory. According to U.S. Pat. No. 8,708,495 B2, these displacement vectors represent a quantitative diagnosis of the geometry of the macular degeneration of the patients studied, however, in practice, they represent only an approximation of the pathophysiological status of AMD.

U.S. Pat. No. 5,589,897 also describes a method and an apparatus for detecting field distortions using an Amsler grid, where the horizontal (or vertical) lines are not displayed to the patient at the same time, rather, the test starts with a line through the focus point and then more lines are displayed at a spacing of 2-5°. This display of individual lines enhances the phenomenon of "fill in" by the brain, whereby distortions that are perceived when a field filled with lines is presented (as with AMD) may not be noticeable when individual lines are observed.

In column 9 (lines 14-17), U.S. Pat. No. 5,589,897 claims that the amplitude (line spacing) and location (method not described) of the distortions can be measured, however, a statement cannot be found as to whether and how the expansion of the qualitatively determined distortions can be quantified.

Furthermore, according to the teaching of U.S. Pat. No. 5,589,897 a control for the distance between the eye and the screen is not provided, so that the distance of the displayed lines is a function of the size of the screen and the distance between the eye and the screen.

U.S. Pat. No. 5,892,570 discloses the detection of metamorphopsia on a computer that displays a deformable Amsler grid on a screen where the subject can "neutralize" distortions he perceives by applying an input with a mouse. The neutralization is performed by moving different intersections points (the nodes of a grid used) on the line perceived as distorted until the line appears straight again. According to the inventors, the described method creates a geometrically opposed pattern, which, from the mathematical perspective, represents a function that inserts an ideal image into a distorted image. In this way, metamorphopsias can be made visible—more precisely approximated. Quantification of the data obtained is not addressed. In particular, U.S. Pat. No. 5,892,570 does not measure or calculate indices; only Figurative storage of the distortion and field loss is at issue. Thus, the test according to U.S. Pat. No. 5,892,570 is not an actual measurement of metamorphopsia, but an assessment of the pathophysiological conditions that may be far removed from reality.

One reason for this is that according to U.S. Pat. No. 5,892,570 (column 10, line 50-62) the values between the nodes of the grid cannot be integrated because information on the distortion between the points is absent and cannot be documented.

In addition, the teaching of U.S. Pat. No. 5,892,570 does not consider the physiological fact that central changes affect quality of life more strongly than peripheral ones.

Further, although U.S. Pat. No. 5,892,570 describes (column 6, lines 20-25) that the spacing between the grid lines should appear to the patient at an angle of 1°, U.S. Pat. No. 5,892,570 does not disclose how a line spacing of one degree is to be ensured.

The inventors of the present application, [Daniela Claessens and Ronald Krüger: AMD—A Metamorphopsia Detector, Poster Board No: 4109-B0031, ARVO Annual Meeting, Denver, Colo., USA, May 6, 2015] report in their poster—without providing details—on a possibility of making metamorphopsia measurable with the help of a computer program based on the Amsler grid. According to the cited Abstract, the software used employs the concept of a negative image, where a distorted image can be straightened by moving a mouse. The degree and extent of the distorted lines or scotomas are transformed into indices with higher weighting placed on findings in the central area of the retina.

The abstract and poster of Claessens and Krueger 2015 does not disclose any indications on how such as a distorted grid can be straightened and/or on how the calculation of the indices or the weighting with respect to the location of the visual field disturbance is performed. In addition, the source code for the software was not provided at the ARVO conference or elsewhere; thus, the disclosure according to Claessens and Krüger 2015 cannot be reproduced by the skilled person without knowledge of the present application.

Based on the state of the art in form of the above abstract by Claessens and Krüger, 2015, it was the object of the present invention to provide a simple and reworkable test that with respect to disorders in the field of vision, allows to make an assessment on the location and a quantitative assessment of the severity and/or progression of a disorder in the field of vision and of distortions.

The present invention relates to a device for quantitative detection and/or monitoring of disorders in the field of vision of an eye of a subject comprising:

a display device;

at least one control device for the display device, and at least one processor and at least one memory device, where the device transmits to the display device a square reticule consisting of a plurality of equidistant parallel horizontal lines and a plurality of equidistant parallel vertical lines arranged with a defined distance to one another (expressed in degrees depending on the viewing distance) and an essentially centrally arranged focus point, where each individual line of the square reticule can be modified by at least one input signal to form a curve that is suitable to transform the nonlinear reticule perceived as curved, due to the disorder in the field of vision of a subject, into the original square reticule again, where the boundary lines of each individual field of the square reticule are defined by boundary functions, which in an initial state are each displayed as lines so that the individual fields are geometrically present as squares and are displayed as such by the display device, but are perceived by subjects with disorders in the field of vision as partially curved; and the boundary lines perceived as curved are modified by a series of input signals, which modify the boundary curves defined by the boundary functions in such a way that the original linear reticule is perceived, where the geometrical deviations, caused by transformation of the regions of the square reticule perceived as curved, from the originally present squares are determined quantitatively as the sum of the absolute values of the horizontal deviations and as the sum of the absolute values of the vertical deviations.

The invention further relates to a method for the quantitative detection of disorders in the field of vision of an eye of a subject, where a square reticule consisting of a plurality of equidistant parallel horizontal lines and a plurality of equidistant parallel vertical lines arranged with a defined distance to one another (expressed in degrees depending on the viewing distance) and an essentially centrally arranged focus point is displayed on a display device;

each individual line of the square reticule can be modified by at least one input signal to form a curve that is suitable to transform the nonlinear reticule perceived as curved, due to the disorder in the field of vision of a subject, into the original square reticule again;

the boundary lines of each field of the square reticule is defined by boundary functions, which are each displayed in an initial state as lines, and are displayed as such by the display device, but are in part perceived by the subject with a disorder in the field of vision as curved; and the boundary lines perceived as curved are modified by a series of input signals, which modify the boundary curves defined by the boundary functions in such a way that the original linear reticule is perceived again, where the geometrical deviations, caused by transformation of the regions of the square reticule perceived as curved, from the originally present squares are determined quantitatively as the sum of the absolute values of the horizontal deviations and as the sum of the absolute values of the vertical deviations.

It was found that it is advantageous to implement the present invention with boundary functions selected from the group consisting of: splines, B-splines, non-uniform rational B-splines, cubic splines, Bézier curves, quadratic, cubic or mixed-rational Bézier curves; Bernstein polynomials; polynomials of 2nd degree or greater; polygon chains; polygon chains calculated using the De-Casteljau algorithm; other algebraic curves, in particular exponent, root, rational and mixed-rational, transcendental functions, in particular exponential, logarithmic, trigonometric, hyperbolic, arcus and area functions.

These functions reliably make possible an optimal numerical approximation and adaptation of distortedly perceived individual lines of the original square Amsler grid.

The feasibility of the present invention is shown below using some exemplary boundary functions without, however, being limited thereto:

1. The "open path" (math.: Open Jordan curve) may, for example, consist of 10 cubic Bézier curves per level open polygon chain and the same number of cubic Bézier curves per horizontal open polygon chain. The curve spacing must be selected such that they are each spaced e.g. 1° apart from the perspective of the eye being examined. The Bézier curve consists of a starting point, two control points, and an endpoint in the plane. Depending on the position of the input signal, all four points are moved in orthogonal direction relative to the initial alignment of the line. The index is calculated from the sum of the absolute values of the deviations of each point in orthogonal direction relative to the "zero point" (undistorted).

2. Open polygon chains having, for example n=10 lines: The n lines are positioned such that they form 10 vertical and 10 horizontal lines (open polygon chains) in the grid (see FIG. 5.). These vertical open polygons chains are each spaced 1° apart, for example. The same applies to the horizontal open polygon chains. Depending on the respective input signal, the starting and ending points of the lines are moved relative to their starting positions in orthogonal direction in such a way that they continue to form an open polygon chain (see FIG. 5, point $H_{(3,39,2)}$ is not moved, points $H_{(3,30,2)}$ to $H_{(3,39,1)}$ are moved). This continues until the subjects no longer perceive a vision distortion. A polygon chain consisting of n=10 lines could lead to a visual impression in which distortion is still present. An open polygon chain with n=100 lines would further increase the "resolution" and provide subjects with the opportunity of adapting the open polygon chains to their visual impression such that they no longer perceive a line as distorted.

3. Polynomial by polynomial interpolation: first, the grid is created from points in horizontal and vertical positions at intervals of 1°. For this 20° wide and 20° high grid, n=200 horizontal and vertical points are defined for each horizontal and for each vertical polynomial. A polynomial of the maximum number of points moved relative to the starting position in orthogonal direction+1st degree is calculated, for example, using Gaussian elimination, Newton's method or the Lagrange interpolation formula. A point is moved orthogonally by the input signal, and a polynomial of the maximum number of points moved relative to the starting position in orthogonal direction+1st degree is calculated. Example: If 5 points are changed by the input signal, a 6th degree polynomial is calculated.

This polynomial is continuously differentiable, which allows determination of an index on any point of the curve by summation of the slope. This can be applied to the entire line (=1 interpolation polynomial for 20°) or to a portion of the grid (n=number of grid segments=number of interpolation polynomials) so that the amount of computation needed for polynomial interpolation can be reduced.

4. Description of an open path with trigonometric functions: the sine function consists of a starting point and an ending point (section of the sine curve path). In the "initial position" (line) the total open path consists of, for example, screen resolution/2 sine functions (e.g., n=1000), with the paths spaced 1° orthogonally to the path. Depending on the position of the input signal, the sinusoidal lines to the left and right next the sine curve nearest to the input signal are removed, and the starting point of the selected sinusoidal line is placed on the starting point of the sinusoidal line to the left. The ending point of the selected sinusoidal line is analogously placed on the ending point of the right sinusoidal line. To obtain a continuous "transition point," the curves to the left and right next to the new sine curve must be replaced by tangent functions and their starting and ending points calculated in a sensible way. This results in a path consisting of n−4 sinusoidal lines+2 tangent functions and indicates a "distortion" at the selected point. Calculation of the index: The lengths of the sine curve sections differing by 1 can be summed to determine an index denoting the degree of distortion. Weighting the location in the grid is also possible by determining the distance between the starting and ending points of the sine curves from the center point.

Based on the above-described explanation of the present invention using several exemplary boundary functions, the skilled person is able to use the other aforementioned mathematical functions as well in order to carry out the present invention.

An advantageous embodiment of the device according to the invention is an embodiment where the device is configured as a PC, a notebook, a tablet computer or a smartphone. These devices allow the subject to easily maintain the correct angle to, and the optimum read distance from, the display device, so that misinterpretation or incorrect grid lines movements caused by incorrect positioning, an unsuitable visual angle, or an incorrect distance can be largely avoided by the choice of the device.

Further, the mobility of the devices used is, of course, particularly advantageous, because this makes the test system available any time and any place, as needed.

For purposes of the present invention it is assumed that the employed devices, in particular, PC, notebook, tablet computer or smartphone are network enabled and equipped with the usual interfaces to the Internet, such as Bluetooth, LAN, WLAN, high speed telephone network, e.g., LTE, according to the state of the art in 2015, however, data transmission paths specifically adapted to the present invention, e.g., own cables and/or connectors and/or wireless paths with their own transmission frequencies, own signal modulation, and transmission protocols are conceivable.

In an advantageous embodiment, at least one camera is provided on the device. This has a number of benefits: for example, an automatic detection of the eye to be examined can be determined by corresponding integrated software. Further, optimal positioning of the device and/or test subject can be detected by the software, and suggestions can be given to the subject on correcting his position and/or on the positioning of the device.

Another aspect is that with telemetric transmission of the data to the treating ophthalmology practice or clinic, for example, the identity of the subject can be automatically determined by face recognition and assigned to the tested subject by local patient data management software on the receiver end.

In an advantageous embodiment, at least one ultrasonic or infrared distance sensor is provided on the device. It can ensure the optimum distance between the subject and the screen, so that the distance of the lines can be displayed correctly in ° degrees, or—when the distance is changed—correctly tracked.

As the examination of a subject with the device according to the invention requires one eye to always be covered—for neurological reasons, as explained above—it is advantageous if covering means are provided for the eye that is not being examined. This may be, for example, an external eye patch. However, distance and/or positioning means with light impermeable coverings that can be attached to the display device can also be used for this purpose.

A further preferred embodiment of the present invention is an embodiment in which retina and/or iris scans are provided to identify the subject and to unequivocally assign the examined eye to the subject. In this way, highest certainty of avoiding incorrect assignments is achieved. Eye-tracking can be used to check whether the examined eye is actually focused on the centrally located focus point, and if deviations occur, the grid is repositioned.

A particularly advantageous device of the present invention is a device designed as eyeglasses, in particular as a diving mask, where display devices are provided instead of eyeglass lenses.

This device is operated by an input device corresponding to the prior art of 2015 that can be moved on a plane to simulate a pen input or by drawing with a finger (mouse, electronic pen or the like).

Such an embodiment allows to utilize all of the advantages of the device according to the invention. For example, the correct positioning, similar to video glasses or a head-up display, is already determined when the device is put on. With suitable covering means provided for one eye, the eye to be examined can be automatically determined, and an integrated camera can be used to assign the measured field of vision data to the subject through face recognition and/or iris and/or retina scans which can be transmitted, for example, via a cryptographic algorithm (with a key exchange corresponding to the state of the art of 2015) to the treating ophthalmologists via Bluetooth, LAN, WLAN, high speed telephone network, such as LTE, etc.

A particular advantage of the device according to the invention is achieved when the transformation-related geometric deviations are determined independently of the boundary function. This ensures that the measured distortion corresponds to the subject's visual impression.

The device according to the invention makes it is possible to calculate a distortion index and/or a visual field loss index (scotoma index) from the determined horizontal and vertical deviations. On the one hand, such an index allows the treating ophthalmologist to quantitatively measure the severity of a disorder in the field of vision in one eye or both eyes of a subject, and/or on the other hand to monitor an already initiated therapy and to quantify the progress of therapy, for example, in cases with wet AMD requiring periodical intraocular injections of anti-VEGF. This device also allows patients to check their visual impressions with respect to field of vision losses and distortions between ophthalmologic examinations and—if an increase of an index indicates worsening—to have an eye examination performed earlier than originally planned.

Since the quality of life depends significantly on a person's visual function [11-12], it is particularly important to detect such disorders in the field of vision that are located in the retinal area of greatest visual acuity and best color vision, i.e., in the region of the yellow spot (Macula lutea) or in close proximity to this area. In order to obtain an additional parameter for this visual function-based quality of life, a preferred embodiment of the device allows weighting the distortion index and the visual field loss index as a function of the distance to the focus point, where disorders that are closer to the focus point are weighted more heavily. In addition, the amplitudes of the distortions are weighted above average and the size of the distortion region below average. This allows making a statement on a subject's vision-related quality of life.

An advantageous embodiment of the device according to the invention is characterized in that changes in size of areas affected by the disorder can be represented by equation (1):

$$\text{Total deviation} = Lg_B(1 + \text{horizontal deviation} + \text{vertical deviation}) \tag{1}$$

where $Lg_B$ is the logarithm base B with B>1, where $Lg_B$ is in particular the natural logarithm, where an eccentricity is given according to formula (2):

$$\text{Eccentricity} = \sqrt{((xF_b/2)^2 + (y - F_b/2)^2)} \tag{2},$$

where $F_b$ is the field width (width of the grid), x is a horizontal coordinate and y is a vertical coordinate of a point in the grid field observed;

where
according to equation (3), a horizontal deviation of a point from the undistorted line is defined as:

$$\text{Horizontal deviation} = \Delta x / \text{eccentricity}^2 \quad (3),$$

and where according to equation (4) a vertical deviation of a point from the undistorted line is defined as:

$$\text{Vertical deviation} = \Delta y / \text{eccentricity}^2 \quad (4),$$

where $\Delta x$ and $\Delta y$=deviation from the original value on the undistorted line.

The field of the present invention is in the detection and/or monitoring of visual disorders. In particular, the device according to the invention uses the idea of a negative image: An image of a square grid perceived as distorted by a subject or patient, can be "adjusted" through one or more input signals actuated by moving a mouse or touching or activating another input device so that the subject can now perceive the grid as a linear grid again. The degree of distortion and the coordinates of the distorted lines and/or the visual field losses are converted into indices to obtain a quantitative measurement of the visual field disorder. Distorted lines are stored in the memory device of the device according to the invention in an array of approximation curves.

Optionally, telemetric transmission of the measured field and/or of the computed measurement values and/or indices as a measure of distortion and/or as a measure of the subject's current visual field loss can be transmitted to the ophthalmology practice, e.g., via end-to-end encrypted email communication (for example, by means of RSA and/or AES encryption).

The device according to the invention thereby ensures the focus by means of a camera, automatically identifies the examined eye, and provides the correct line spacing in degrees by means of an ultrasonic sensor.

With the help of the device according to the invention, it becomes possible on the one hand to quantitatively measure metamorphopsia—the most striking symptom of macular edema—and visual field losses—symptomatic of, for example, wet or dry AMD and glaucoma—and on the other hand, with existing eye diseases, to monitor the appropriate course of therapy, the progression of the disease, or the therapeutic success and to adapt them if necessary.

A particular advantage of the present invention is that patients can use the device themselves—without ophthalmological support—to perform a "home test" and forward the measured and computed data in electronic form to the treating ophthalmologist at any time. The device and method according to the invention can alternatively also be used as a mobile test at an optician center, by a family physician, or occupational health physician for prophylactic care.

The software of the device according to the invention is based on the Amsler grid [10] [Marc Amsler: The investigation of qualitative vision with the square grid. Instructions for use of test panels. Theodore Hamblin LTD, London 1958]

As already mentioned in the introduction, the Amsler grid consists of a box on which a grid of horizontal and vertical lines is arranged as a square grid. The subject to be examined must observe the grid—after covering one eye—with the uncovered eye and describe the location of the distortion to the ophthalmologist. As a result, the ophthalmologist receives only a qualitative statement about any field of vision distortions and/or losses. As quantitative data are not collected by this conventional test, the measurement and the monitoring of disorders of the field of vision using the classic Amsler grid are only qualitative in nature and thus limited.

The invention the present application is based on, and in particular the inventive method that can be implemented as software uses the concept of a "negative image" of field of vision disorders in a human eye.

An image of the test grid perceived by the patient as distorted can be moved back to the original square grid by modifying the gridlines perceived as distorted using movement with an input device, such as a mouse, or a finger, or a pen, on a device according to the invention, configured as a PC, touchpad, or smart phone, or a special input device. To this end, the subject or patient changes the perceived curved lines with the input device until they appear linear again. A healthy eye would therefore effectively see a distorted "negative image" of the Amsler grid. The present invention then allows to quantitatively capture the degree, the localization and the dimension of perceived metamorphopsias and to convert distortions and/or or scotomas by means of the "negative image" into indices which then measure the present field of vision disorders, and to monitor previously initiated treatments.

It has been surprisingly found that the inventive method correlates extremely well with the conventional methods for measuring scotoma on the one hand and metamorphopsia on the other. When the data on visual field losses obtained with conventional computer perimetry are compared with those determined with the device according to the invention, the location of the scotoma (see. FIG. 3) agrees between both methods.

The same applies when images of the diseased retina created by the current gold standard, optical coherence tomography, are compared with the distorted images or the corresponding metamorphopsia data obtained by means of the device according to the invention and method, as shown in FIG. 2.

The present invention is employed not only for the diagnosis of retinal diseases but also for monitoring therapies for retinal diseases that have already been initiated. The AURA [13]-, COMPASS [14]- and WAVE [15] Studies have shown that patients were neglected in clinical practice when diagnostic procedures were used, and not enough injections were administered for treatment of chronic retinal diseases. The latter was caused by logistical problems, suboptimal compliance, and lack of adherence to treatment, or simply because the patient did not notice a worsening of visual symptoms or noticed them too late. According to the aforementioned studies, diagnoses made too late and low therapy frequencies led to poorer therapeutic results compared to optimized diagnostic and therapeutic conditions than should actually be possible with the modern ophthalmology options available [15] [13-14]. [Finger, R P, et al.: Treatment Patterns, visual acuity and quality-of-life outcomes of the WAVE study—a non-interventional study of ranibizumab treatment for neovascular age-related macular degeneration in Germany. Acta Ophthalmol, 2013, 91 (6): p. 540-6, Holz, F G, et al, Multicountry real-life experience of antivascular endothelial growth factor therapy for wet age-related macular degeneration, Br. J. Ophthalmol 2014.; Wolf, A. and A. Kampik, Efficacy of treatment with ranibizumab in patients with age-related macular degeneration in routine clinical care: Data from the COMPASS health services research. Graefes Arch Clin Exp Ophthalmol, 2014. 252 (4): p. 647-55.].

The present invention can support the ophthalmologist with diagnosing and evaluating OCT images, as the OCEAN study [18] or its subgroup in the ORCA module and the CATT study [19] have shown that approximately 30% of OCT images are not correctly interpreted by the treating ophthalmologist.

The device and method according to the invention allow the subjects or patients to perform frequent screening and monitoring themselves, as the device is easy to use, affordable, and available to most people through the use of existing mobile or stationary devices.

The present invention now for the first time allows on the one hand early detection and treatment of pathophysiological disorders of the eye accompanied by visual field distortions and/or visual field losses in cases with an existing initial suspicion or known risk, for example, familial dispositions, underlying disease (diabetes, myopia, HIV infection, pseudoxanthoma elasticum) or nicotine abuse, and on the other hand close monitoring—with as few as possible visits to the doctor—of the therapeutic measures over time.

The device according to the invention was therefore particularly designed to provide a tool set that the patients can use themselves as mobile or home monitoring devices to monitor their disease progress, but also as a highly accurate diagnostic tool for the experienced ophthalmologist in daily practice. With the device according to the invention and the inventive method, it has become possible for the first time to not only qualitatively detect metamorphopsia and scotoma with simple means, but also to quantitatively measure them, to quantify their severity, and to precisely determine their location and dimensions.

A particular advantage of the present invention is that, due to its ease of use, the patient can use the device according to the invention to perform a field of vision test at home.

The device and method according to the present invention can monitor the patient's adherence to treatment intervals, for example, intravitreal injections in cases with wet AMD, or provide early indications for the need for increased frequencies of therapeutic measures.

By means of the present invention, an earlier diagnosis of macular edema or visual field losses can be made, and indications of recurrences can be documented at an early stage, in part by the patients themselves.

A special economic aspect of the present invention is based on the fact that the device according to the invention plays a role as an instrument of public health in remote areas without easy access to specialized ophthalmology care. In particular, it can support an early diagnosis and monitoring of macular disease in such areas especially.

In addition, future treatment options for macular diseases—in this case of eye drops to be applied by the patient—require an even higher patient treatment compliance. These future therapies indicate a need for an increased monitoring frequency of symptoms, which can be performed using the present device.

Over time, the present invention can contribute to achieving optimal therapeutic results, to reducing the number of avoidable visual disorders and blindness, and to increasing the quality of life of those affected when the number of patients increases who use the present invention for instructed self-diagnosis and monitoring.

Due to the aforementioned economic relevance of macular diseases, the present invention can also make an important economic contribution, at least with respect to early detection and treatment monitoring of AMD.

The present invention allows to quantify visual distortions. In particular, it is possible to create an index that captures the degree, area and location of distortions and field of vision deficits. The results can, for example, be stored in an encrypted (AES-256) data array and be shared by both the patient and the treating ophthalmologist.

In one embodiment of the present invention, monitoring is carried out using a mobile device, where it is preferable that the measurement is performed using a handheld device, such as a tablet computer or a smart phone.

A further embodiment relates to monitoring using a stationary device, which is provided, for example, in an ophthalmology office with access to the patient data management system and other diagnostic devices.

In a further embodiment, the invention provides a method for assessing and/or treating a patient suffering from disorders in the field of vision.

Eye diseases that cause distortions include those leading to macular edema. These include, for example, but are not limited to, choroidal neovascularization, age-related macular degeneration (wet and dry forms), macular edema in cases with retinal vein occlusion (RVO) including branch retinal vein occlusion (BRVO) and central retinal vein occlusion (CRVO), choroidal neovascularization secondary to pathological myopia (PM), diabetic macular edema (DME), uveitis or pseudoxanthoma elasticum, retinal pigment sheet separation in cases with e.g. central serous chorioretinopathy. Diseases in other areas of the retina (epiretinal gliosis, macular (layer) hole) or other structures of the eye, e.g., the cornea, such as, for example, corneal scars or keratoconus can cause metamorphopsia.

In cases with wet AMD, the patients' treatment responses, for example, can be monitored by the patients themselves using the present invention, and in addition by the optician and/or optometrist as needed, optionally by telemetry, in order to provide the patients with an indication of whether and when the next treatment is required.

Thus, the treating ophthalmologist can tailor the treatment plan for a patient and adjust the therapy to the individual patient, thus providing the patient with the maximum therapeutic benefit with minimal risk.

Likewise, the present invention can optimize the efforts and costs of the parties concerned, in particularly health insurances, patients, and their relatives.

Remote Monitoring

For the purposes of the present invention, the term "remote monitoring" is to be understood as meaning that the patients themselves decides which data they would like to share, for example, with the ophthalmologist of choice. The patient can transmit patient-relevant data, for example, by sending encrypted e-mails with a correspondingly encrypted attachment. Depending on the results of the data evaluation by the specialist physician who evaluates the patient's field of vision data, other therapeutic and/or diagnostic procedures can then be recommended. Based on the longer-term trend of the test results, taking into consideration their other assay test results, AMD patients can, for example, be advised to end or continue a therapy, to have diagnostic measures performed, and dosage recommendations for administration of pharmaceuticals can potentially also be given.

As already explained, the present invention is ideally suited for use on mobile devices.

The device according to the invention is generally operated via a display, cursor control, and an interface. The device may further comprise a camera. Thus, on the one hand the device can individually identify the patient, and on the other hand automatically detect which eye is being examined, and whether the eye is focused on the center of the test field (eye tracking), which allows the entire grid to be tracked. The device may also comprise an ultrasonic distance sensor, which ensures that the subject has the correct distance to the screen needed to automatically display the correct line spacing in degrees on the screen.

Preferably, the display of the device according to the invention is designed as a touch screen so that the patient can make entries directly on the screen. This should particularly appeal to elderly patients, since neither a keyboard nor a mouse must be used, which often cause anxiety and rejection in elderly patients.

In a preferred embodiment of the present invention, the display device meets one or more of the following standards: (A) for background luminance (i.e., it falls within the range between 80-320 Cd/m$^2$), (b) a contrast ratio of 300:1, 600:1 or greater, in accordance with ISO 8596, and (c) ISO 8596: 1994 (E) (i.e., has a color temperature of 2500K to 7000K).

In another preferred embodiment, the device comprises a camera that faces the patent while the test is being performed. The device may initialize facial recognition software that, in combination with the camera, (a) allows the device to confirm the identity of the patient and the completion of the test (iris recognition, retinal scan), Further, the camera allows to determine whether the correct eye is being tested (i.e., that the patient has closed or covered the other eye).

In order to identify the patient, the camera can also, for example, recognize the typical nasal and temporal retinal vessel formation, and the device can analyze this data for purpose of identification.

Further, the camera can also monitor a constant, preset distance from the patient's eyes necessary for the test, and if the distance is too far or close sound a warning.

In particular, such warnings, information, or advice regarding, for example, suitable corrective glasses, distance to the device, etc. can be displayed on the screen or, preferably acoustically announced for visually impaired patients via text-to-speech software.

In a further embodiment, the device according to the invention may also measure the distance between the patient's eyes and the device and adjust the test accordingly. Thus, if the device is positioned closer to or further away from the patient, the size of the grid used in the test may be adapted to ensure that the angle between two initially parallel lines is x° degrees (e.g., 1° degree).

A distance measuring device may be implemented by non-contact sensors, for example, by the use of ultrasonic or infrared sensors, or also by a defined distance determined by the hardware, for instance by means of a mechanical spacer.

In a further embodiment, the patient may wear an eye patch over the eye that is not being tested.

In another preferred embodiment, the device may further comprise a microphone, a speaker, and voice recognition, and text to speech software. Thus, the device could be operated by the patient using voice commands and by speech instructions, information, and warnings the device receives.

The present invention has the following further advantages and characteristics:

1. Parameters amplitude, eccentricity, and area

The users themselves produce a distorted picture: this (negative) image precisely reflects their distortions: for distortions, the amplitude, eccentricity, and area are measured by individual values and calculated. For visual field losses, the values area and eccentricity are measured and calculated.

For distortions and visual field defects the vision quality-related total index is further calculated for each case:

Central changes are weighted higher than first peripheral changes in the previously (almost) unaltered grid/field of vision than later ones in the already distorted grid, or when deficits in the field of vision already exist (mathematical method, e.g., log delta).

Since visual impressions are psychometric functions (comparable with an indication of visual acuity=visus, cf. Michael Bach and Guntram Kommerell https://www.uniklinik-freiburg.de/?id=3713)), in the present invention the logarithm of the parameter "amplitude" is used to calculate the total index.

As the logarithm of eccentricity is used to calculate horizontal or vertical deviations, it is weighted higher (the more central, the higher the weighting) in the calculation of the eccentricity index and the total index, reflecting its physiological significance. This reflects the fact that distortions located centrally in the field of vision have a significantly higher effect on the quality of life than peripheral ones. If a central distortion is perceived in a text, exactly the syllable to be read or the spot in an image to be viewed (e.g., the eyes of another person) is always distorted. Since the density of nerve cells (cones), which enable sharp vision and color perception, is highest in the center of the retina (fovea=point of highest acuity), a distortion in this area has a particularly high compromising effect: sharp vision is impaired, objects appear distorted.

2. In order to ensure reproducibility on different sizes of screens, and to allow intra- and inter-individual comparisons of measurements, the lines according to the invention are always specified at a distance of x degrees, preferably in a range between 0.5° and 2°, in particular 0.5°; 1° or 2° and not displayed at a specified distance in mm on the screen. The line spacing in degrees always results from the distance between the eye to be examined and the screen, which can be determined by a known ultrasonic measurement, for example.

The size of the field of vision to be detected results primarily from the screen size and secondarily from the distance between the eye and the screen.

3. Measurement of visual field defects

According to the invention, visual field losses can be marked and measured. The visual field loss is detected as a total index. The overall index reflects the size of the visual field loss and its location: central losses lead to a higher index than a peripherally loss of the same size.

The combination of metamorphopsia and field of vision documentation increases the sensitivity for detecting pathological changes in the central retina (macula) because not only diseases can be detected that lead to distortions, but also more advanced stages of the disease that lead to visual field losses and/or poor visual acuity or reduced contrast sensitivity.

4. Technical distinction: point of intersection/node versus any point in the grid moveable/changeable The possibility of changing all points of the boundary lines in the grid displayed to the patient according to the invention, enables the present invention to produce—in contrast to the aforementioned prior art cited—a realistic image of the negative image of the distortion; therefore, it considerably more accurate than conventional methods.

In contrast to the prior art, the display using the inventive method not only allows to approximate the visual impression, but an exact display of the negative image of the visual impression can be entered as curves, instead of only moving intersection points within a grid.

Further, focus control, e.g., eye-tracking ensures that distortions are not marked in the wrong location in the field of vision and/or thereby marked or entered several times by the patient.

The inventive method can display distortions even if they pertain to a distance that is smaller than the distance between two adjacent lines. This is particularly important for central distortions (or visual field defects), because affected persons notice them even if they are small. Interpolation between two (e.g., vertical) lines can be achieved by the distortion of orthogonal lines (e.g. horizontal).

Further advantages and features of the present invention will become apparent from the description of embodiments and from the drawings.

FIG. 1 is a section (left upper quadrant) of a distorted Amsler grid; represented by cubic Bézier curves.

FIG. 2a/b is a representation of a field of vision distortion obtained by means of the invention, centrally and to the right of the focus point, and an image of the retina with visible edema in the central retina obtained by means of optical coherence tomography is inserted in the lower right quadrant; and FIG. 3a/b is a representation of a visual field loss obtained by means of the invention, close to the focus point and the same visual field defect obtained by conventional computerized perimeter is inserted into the lower left quadrant;

Figure 3A:
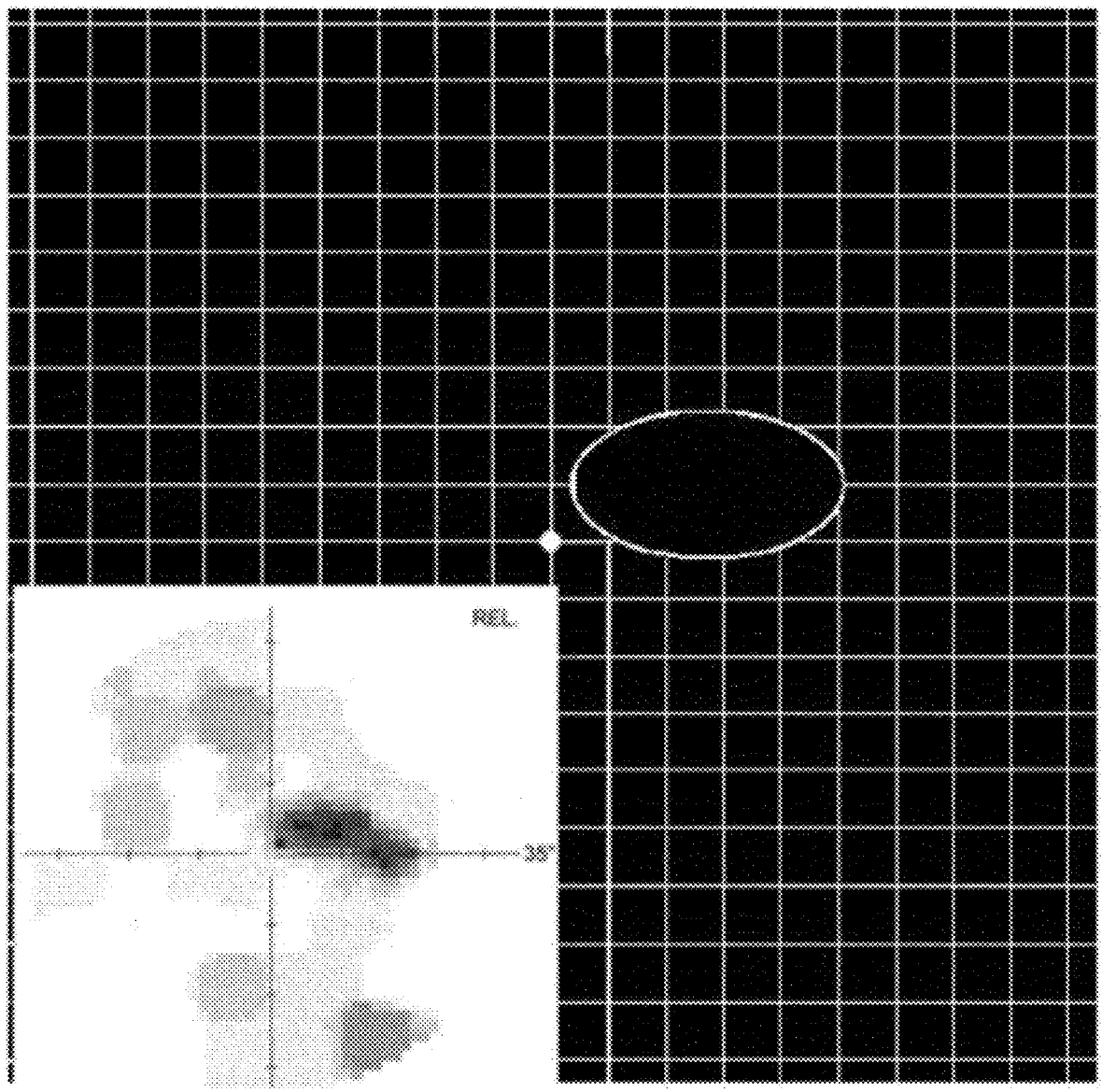
Figure 3B:
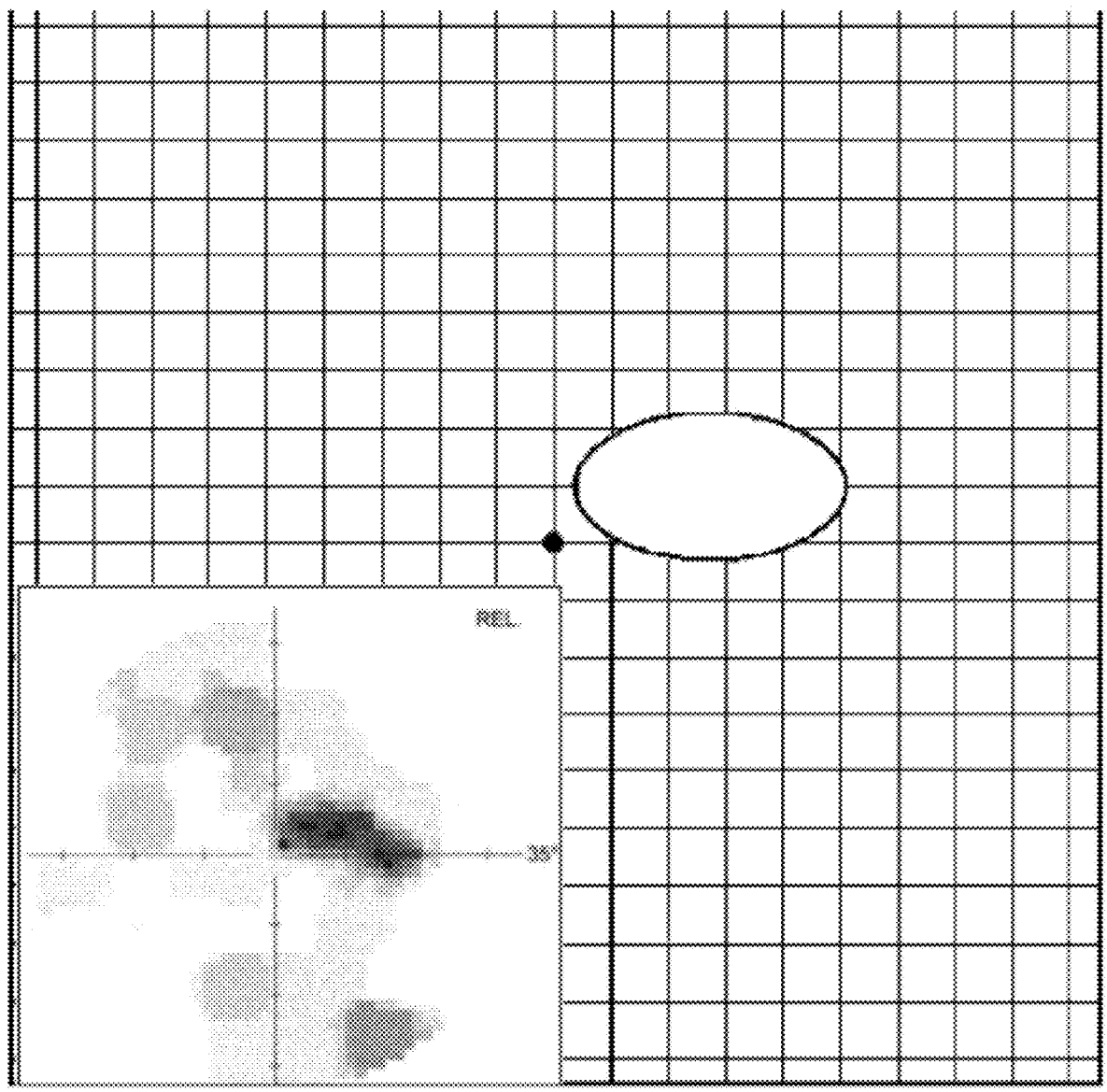
Figure 4:
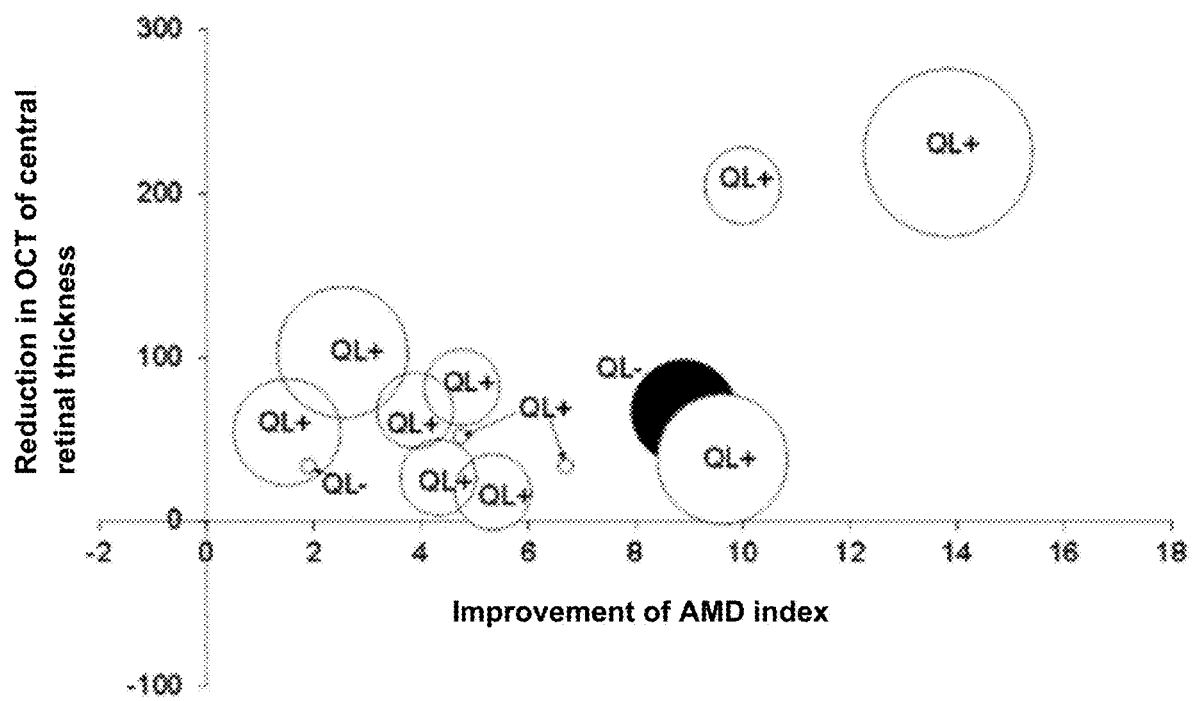
FIG. 4 shows the results of a correlation between the indices of the invention and OCT, VA (visual acuity=best corrected visual acuity) and QL (vision-related quality of life measured by the National Eye Institute Visual Function Questionnaire-25)

A total of 13 patients were examined before and after a treatment cycle (a total of 3 intraocular injections of anti-VEGF in monthly intervals for treatment of macular edema). The test parameters were the metamorphopsia index of the invention described herein, the best corrected visual acuity, spectral domain OCT [16], visual function-related quality of life (NEI VFQ-25) [17], Amsler test [10], retinal wide-angle photography, and retinal examination after pupil dilation. All measured values changed significantly over the course of therapy. The average decrease of central retinal thickness measured by OCT was 77.54 µm (median 55 µm; SD 49.99; Cl 111.74; 43.33), the average decrease in the metamorphopsia index was 6.0 (median 4.76, SD 3.5; Cl 7.9; 4.1). The best corrected visual acuity improved in 9 eyes (FIG. 4 large spheres), worsened in 1 eye (FIG. 4: large sphere Q−) and remained stable in 3 eyes (FIG. 4: small spheres). The average best-corrected visual acuity was 0:38 log MAR (SD 0.28) before and 0.25 log MAR (SD 0.21) after injection therapy (Cl 0.21; 0.03). The index growing with increasing quality of life of the test for detecting the subjectively experienced quality of life NEI VFQ-25 rose in 11 cases (FIG. 4 QL+) (average increase 8.77; median 19; SD 12:39; Cl 17.74; 3.65) and dropped in 2 cases (FIG. 3: QL−): in one of these two cases, the eye additionally developed lens opacity (cataract) during the time period of observation, which decreased the visual acuity; in the other case the field of vision deteriorated in the time period of observation due to glaucoma. With the exception of the two last-mentioned cases, the metamorphopsia index represented the trends that were recorded by OCT, best corrected visual acuity. Amsler test, and NEI-VFQ 25.

To illustrate the method and device according to the invention, a typical examination method is described in the following: In the present invention, the grid display is assembled by a suitable number (5 to 20) of cubic Bézier curves per horizontal or vertical line spaced at a distance of 1° (relative to the distance of the eye to be examined). According to FIG. 1, each curve in the exemplary case is defined by 4 points in the plane: horizontal $H_{(h, 0 \ldots 3)}$, where h corresponds to the number of horizontal lines (1 to n) with n=number of the square fields, and vertical $S_{(V, 0 \ldots 3)}$ where v is the number of the vertical line (1 to n) with n=number of square fields. These lines form the basis of the grid. In the exemplary case, each field of the grid is delimited by 4 cubic Bézier curves.

Each horizontal and each vertical line can consist, for example, of 10 cubic Bézier curves. The points are numbered consecutively: $H(x, h)$ $x=0 \ldots 39$ and $h=0 \ldots 9$. Likewise, the vertical points are numbered consecutively: $S(y,v)$, with $y=0 \ldots 39$ and $v=0 \ldots 9$.

The points $H_{(4,h)}$ and $H_{(3,h)}$ and the points $H_{(7,h)}$ and $H_{(8,h)}$ are coupled. This results in coupling of the fields and an open polygon chain results. In this way, uniform curves can be displayed over the entire field (see FIG. 1).

For example (see FIG. 1.): Line 1: $H_{(3,1)}$ and $H_{(4,1)}$ have the same coordinates, and therefore describe the same location in the grid.

Figure 1:
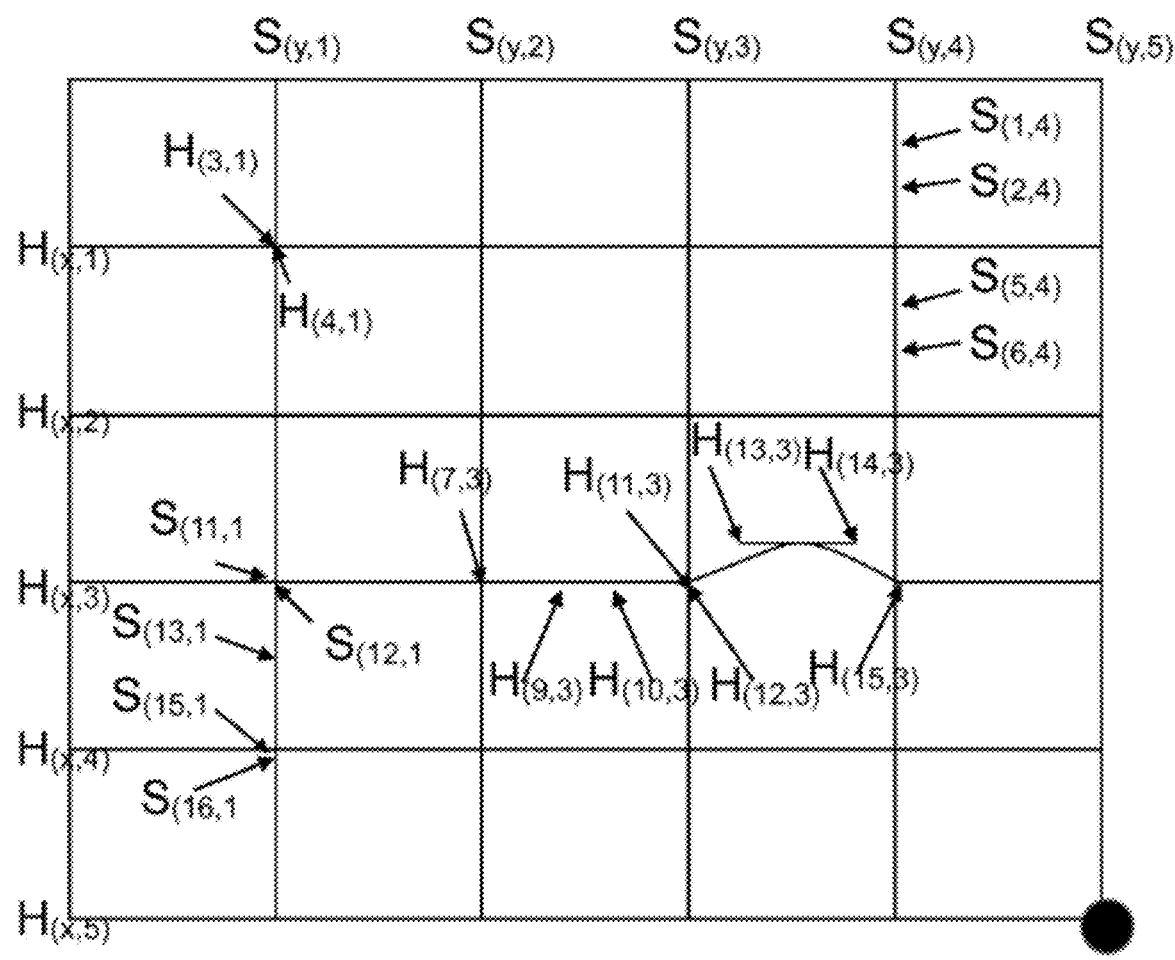
Figure 2A:
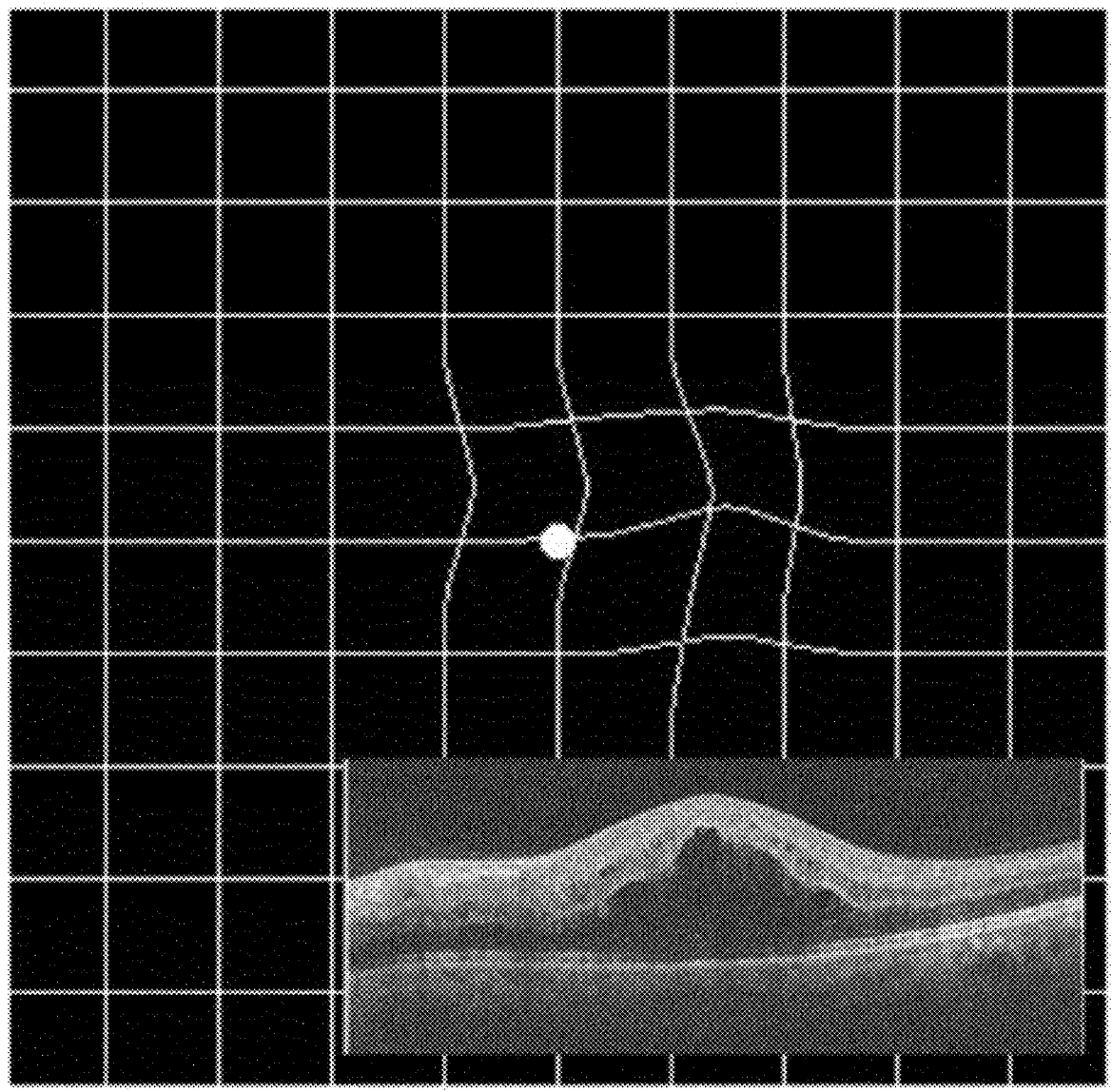
Figure 2B:
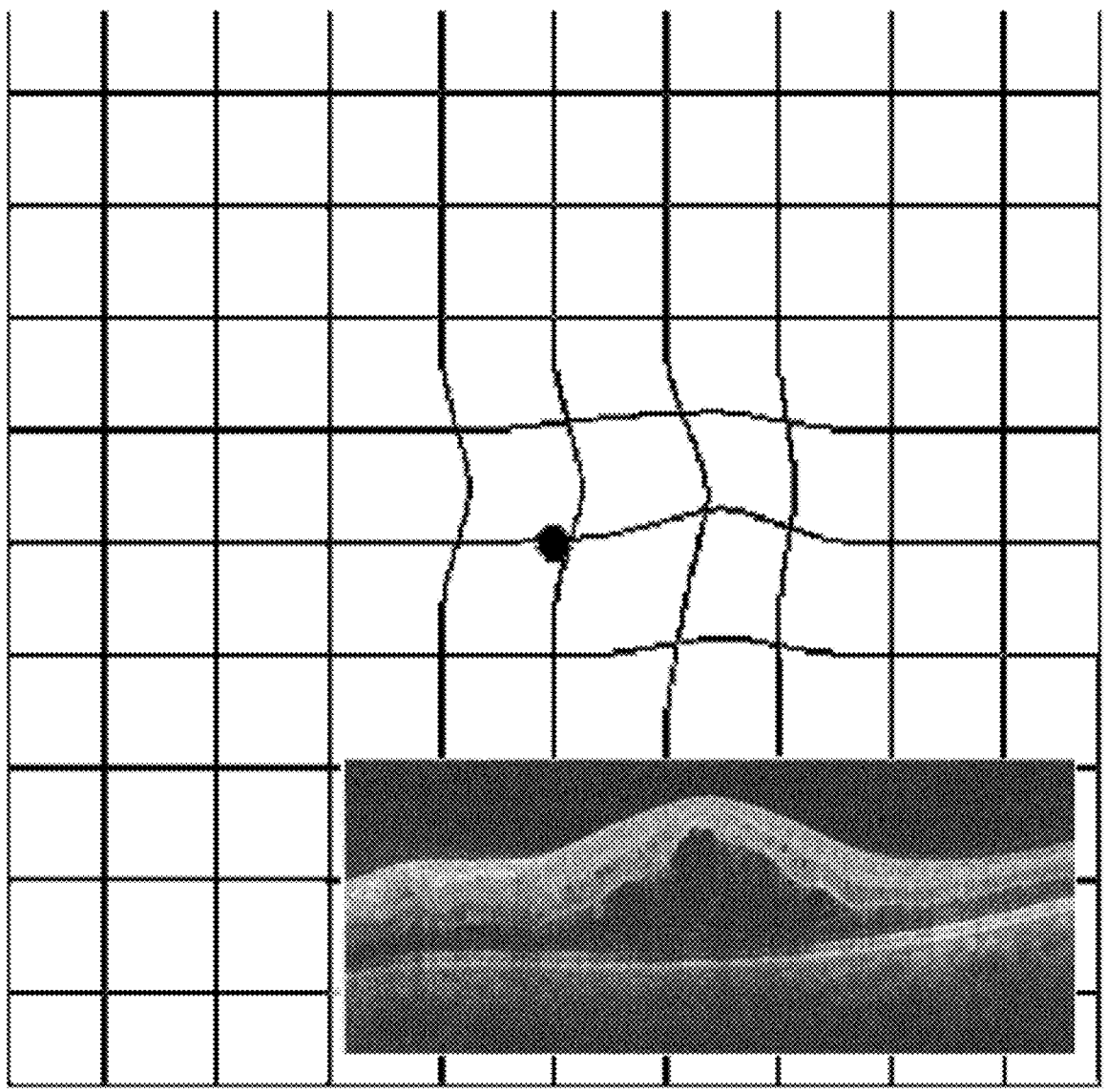

The points $H_{(13,3)}$ and $H_{(14,3)}$ described in FIG. 1 are defined as the control points of the cubic Bézier curve.

To perform the test with the grid defined in the exemplary case described above by cubic Bézier functions, the patient first focuses with one eye on the focus point in the center of the grid (see FIG. 1, bottom right). The device automatically identifies the patient and the examined eye via iris or retina scan, or by detecting the markings on the patch over the eye that is not being examined and recognizes whether the patient is focusing on the center. The patient is prompted to select only one type of lines (horizontal or vertical lines) to display. The next step for the user is to straighten the lines he perceives as distorted using an input device while focusing on the focus point. This can be accomplished using a mouse wheel, a mouse click, a finger, a stylus, or by means of a touchpad.

In a second step, the patient is asked to select the other lines that are perpendicular to those already processed. The user proceeds with these lines as with the other line style. Namely, he straightens those lines he perceives as distorted at exactly those locations where he perceives distortions, again while focusing on the focus point (and while covering the eye that is not being examined).

By the patient "straightening" the curved lines he perceives as curved, a virtually negative or complementary image of his real field of vision results, where on the one hand disorders in cases with scotoma appear as delimited zones, and on the other hand, in cases with metamorphopsia, they appear as visible distortion in the grid. The extent of the distortion and/or visual field loss can then be quantified, stored, and followed over any period of time by calculating a scotoma index and a metamorphopsia index using the cubic Bézier functions in order to monitor the success of an already initiated therapy, and on the other hand to take early therapeutic measures if the pathophysiological condition worsens.

The mentioned indices are derived as follows ($M_g$ and $S_g$ are indices, while the other values are used for calculation):

Metamorphopsia Index (Mg):

$$Ex = \sqrt{\left(x - \frac{Fb}{2}\right)^2 + \left(y - \frac{Fb}{2}\right)^2} \quad (1)$$

Ex=eccentricity;

$$q_v = |x_{deviation}| \quad (2)$$

$$q_h = |y_{deviation}| \quad (3)$$

$q_v$=deviation in the horizontal direction; $q_h$=deviation in the vertical direction $x_{deviation}$ in mm; $y_{deviation}$ in mm $$Dx = \sum_{i=1}^{Fb} \frac{50}{Ex^2 + 50} \quad (4)$$

$$Dy = \sum_{i=1}^{Fb} \frac{50}{Ex^2 + 50} \quad (5)$$

Fb=field width (width of the grid)
$D_x$=deviation in horizontal direction; $D_y$=deviation in vertical direction $$W_1 = \log\left(\left(\sum_{i=1}^{Fb} q_i\right) + 1\right) \quad (6)$$

$W_1$=distortion amplitude $$W_2 = \log\left(\left(\sum_{i=1}^{Fb} \frac{50}{Ex_i^2 + 50}\right) + 1\right) \quad (7)$$

$W_2$=distortion eccentricity $$W_3 = \log\left(\left(\frac{\sum_{i=1}^{Fb*4} VP_i}{(\sum n)^2}\right) * 100 + 1\right) \quad (8)$$

$W_3$=distortion area
VPi=moved Bézier control points
n=number of fields shown, resp. number of vertical or horizontal lines $$M_g = (\log(D_x + D_y + 1) + W_3) * 1.3 \quad (9)$$

Metamorphopsia Index ($M_g$):

The sum of the absolute values of all amplitudes, the eccentricity of each moved Bézier control point (see formula), and the expansion (area) of the field of vision disorder are measured: the measured value is greater the larger the sum of the absolute values of all amplitudes, the more centrally located the field of vision disorder, and the greater the area of the field of vision disorder.

By considering the eccentricity, the fact is taken into account that central disorders in the field of vision are perceived as more bothersome than those located in the periphery. The use of the logarithm in the calculation formulas for amplitude, eccentricity and area reflects that psychometric functions are measured: distortions in previously undistorted images are perceived as more notable than the same distortions in an already distorted image.

The distortion values $W_1$ (distortion amplitude), $W_2$ distortion eccentricity, and $W_3$ (distortion area) can provide the physician or optometrist with further information about the disease or the symptoms.

Scotoma Index $$S_A = \frac{S_x * S_y * \pi * 30}{Fb^2} \quad (1)$$

where $S_x$=Length of the x-axis and $S_y$=length of the y-axis and Fb=field width of the grid $$S_E = \frac{Fb}{2 * \sqrt{\left(Es_x - \frac{Fb}{2}\right)^2 + \left(Es_y - \frac{Fb}{2}\right)^2}} \quad (2)$$

where $F_b$=field width of the grid and
$E_{Sx}$=x-component of eccentricity of the centroid of the ellipse and
$E_{Sy}$=y-component of eccentricity of the centroid of the ellipse
$S_g = \log(S_A * S_E + 1)$
Scotoma Index ($S_g$):

The a) expansion (area) of the field of the vision disorder and b) the eccentricity of the centroid of the ellipse are measured: the measured value is greater the larger the area ($S_A$) and the more centrally located the field of vision disorder ($S_E$).

Regarding the mm versus degree partitioning of the grid=0.1°, 0.5°, 1° and 2°, this allows to adapt to disease-specific factors (either display of a larger field of vision or the option of displaying smaller changes). The number specification of degrees (versus length units, e.g., mm) allows making intra-individual comparisons (monitoring of disease progression), inter-individual comparisons, and standardizations with respect to disease types and stages, regardless of the screen size and resolution.

For example, the following comparison between the index and the clinical classification results from the data collected in the context of the present invention (Beckman—classification of the severity of macular disease):

| Disease stage | Average metamorphopsia index | Average central retinal thickness [μm] |
| --- | --- | --- |
| Advanced macular edema | 3.49 | 329 |
| Minor manifestations of macular disease | 1.06 | 255 |
| Healthy | 0.10 | 264 |

The following stages can be assigned from these results:

| Disease stage | Metamorphopsia index |
| --- | --- |
| Healthy | <0.5 |
| Minor manifestations of macular disease | 0.50-1.50 |
| Advanced macular edema | 1.50 |

The normal retinal thickness is between 250 and 300 μm. In the presence of macular edema, the retinal thickness increases.

Previously unpublished data that were obtained using the present invention (publication DOG October 2016) show that in age-related macular degeneration and diabetic macular edema the (AMD-) metamorphopsia index is a better classifier than central retinal thickness (CRT):

The correlation of the metamorphopsia index and CRT in diabetic macular edema was high (Pearson correlation coefficient 0.733 (p=0.0004) and moderate in wet macular degeneration (Pearson correlation coefficient 0.426; p=0.0028). Since the group with wet macular degeneration included eyes with retinal atrophy (i.e., thin retina) up to less than 200 μm (median 288 μm), the criterion "unhealthy" was more likely correctly captured in these cases by the metamorphopsia index than by the central retinal thickness (CRT) criterion.

Cohen's κ, a measure of the agreement between the metamorphopsia index and CRT, was moderate (DME) at 0.59 or sufficient at 0.22 (wet AMD): It should be taken into account here that in the group with wet macular degeneration, 53% of the eyes had a retinal thickness of <300 μm due to retinal atrophy, and therefore the conclusion "healthy" was made incorrectly when retinal thickness was measured. The sensitivity and specificity for the detection of diabetic macular edema was 100% and 77.78% for the metamorphopsia index and 80% and 89% for the CRT: diseased eyes were better recognized using the metamorphopsia index than using central retinal thickness. In the group including age-related macular degeneration, the sensitivity and specificity of macular edema detection was 100% and 61% using the metamorphopsia index and 59% and 85% using CRT: again, diseased eyes were recognized better with the metamorphopsia index than with the central retinal thickness. In cases with diabetic macular edema and wet macular degeneration, the metamorphopsia index is a more sensitive parameter than the central retinal thickness measurement.

Distortions in the Visual Field

A cubic Bézier curve is defined by the four points $S_{1,4}$ (S=vertical, H=horizontal) (see FIG. 1). Each vertical and each horizontal line of the total grid consists of n=10 cubic Bézier curves with the points $S_{(1 \ldots n, 1 \ldots 4)}$. At the start of the measurement, the points are initialized such that $S_{1,1}$ is located on the coordinate (0|0), and $S_{(1,2)}$ and $S_{(1,3)}$ on the coordinate (0|b/2) (where b=width of the fields, and width of the fields=width of the screen/n, [provided they are smaller than the height, otherwise the height of the screen]) and $S_{(1,4)}$=(0,b). This is followed by the next cubic Bézier curve: $S_{(2,1)}$=$S_{(1,4)}$=(0,b). $S_{(2,2)}$=$S_{(2,3)}$=(0,b*3/2) and $S_{(2,4)}$=(0, b*2). The points of each Bézier curves are calculated as follows:

$$S_{(i,1)}([i-1]*b|[i-1]*b)$$

$$S_{(i,2)}([i-1]*b|[i-1]*b+b/2)$$

$$S_{(i,3)}=S_{(i,2)}$$

$$S_{(i,4)}([i-1]*b|[i-1]*b)$$

where n=10; i=1 . . . n and b=width of the screen/n

For the horizontal points of the grid lines, the points (H) are computed analogously as follows:

$$H_{(i,1)}([i-1]*b|[i-1]*b)$$

$$H_{(i,2)}([i-1]*b|[i-1]*b*b)$$

$$H_{(i,3)}=H_{(i,2)}$$

$$H_{(i,4)}([i-1]*b|[i-1]*b)$$

n=10: i=1 . . . n and b=width of the screen/n

Calculation of the Indices

Degree of Distortions

All points of all Bézier curves are checked to determine whether they are still located on "their" zero line. If this is not the case, the absolute value of the deviation is summed for each point:

| Point | Target | Actual | Deviation | Location |
|---|---|---|---|---|
| $S_{(2,.2)}$ | (b \| b*1/2) | (b \| b*1/2) | 0 | 0 |
| $S_{(2,4)}$ | (b \| b) | (b + 1 \| b) | 1 | 1/5.65 = 0.18 |
| $S_{(3,4)}$ | (b \| b*2) | (b − 1 \| b*2) | \| −1 \| = 1 | 1/5.31 = 0.19 |
| $H_{(5,1)}$ | (b*4 \| 0) | (b*4 \| 0) | 0 | 0 |
| $H_{(5,2)}$ | (b*9/2 \| 0) | (b*9/2 \| 1) | 1 | 1/5.02 = 0.2 |
| $H_{(6,4)}$ | (b*5 \| b) | (b*5 \| b − 1) | \| −1 \| = 1 | 1/4 = 0.25 |
| Sum: | | | | 0.81 |
| 1 + ln(sum) | | | | 0.79 |

The location is the distance from the focus point. This value weights the deviation inversely proportional, since an impairment in the central field of vision is subjectively perceived as worse.

The summation is performed for each point of the Bézier curves in the horizontal and vertical directions. The sum of the absolute values of the deviations is weighted by the logarithmic function base>1. The base depends on the importance of quality of life with respect to the severity of distortion, e.g.;

Severity of distortion=$\log_e$(sum)+1; where $e$=2.71828182845(Euler's number)

Size of the Distortion Area

The number of points moved is a measure for the size of the affected area and is also factored into the overall index by multiplication or addition also with the logarithm base B, depending on the importance for the quality of life.

Field of Vision Loss (Scotoma)

This area is represented by an ellipse. The index for the visual field loss is calculated from the area (A) of the ellipse and the distance (b) between the centroid of the ellipse and the focus point.

$$A=\pi*x*y$$

where π=3.141592654
x=semi-axis in x-direction
y=semi-axis in y-direction $$b=\sqrt{Ex^2+Ey^2}$$

Polygon Chain (Lines)

Figure 5:
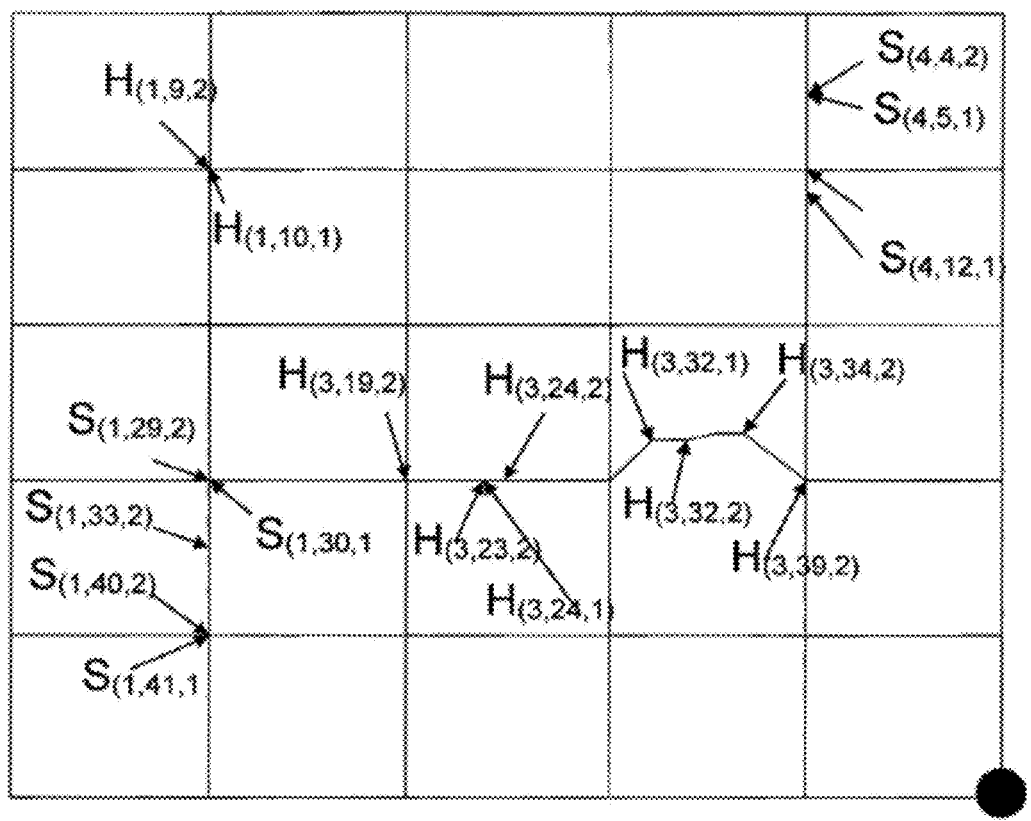
FIG. 5 shows a section (upper left quadrant) of a distorted Amsler grid represented by straight lines.

A line is defined by two points $S_{(i,k,1)}$ and $S_{(i,k,2)}$ (S=vertical=H=horizontal: $H_{(i,k,0)}$ and $H_{(i,k,2)}$ (see FIG. 5). Each of the vertical n=10 and each of the n=10 horizontal lines of the total grid is composed of m=10 and g=n*m=100 lines with the points $S_{(i,k,o)}$ (where i=numerator for the vertical: 1 . . . 10; k=numerator for the line: 1 . . . 100 and o=numerator for the starting or ending point of each line: 1 . . . 2). At the beginning of the measurement, the points are initialized such that $S_{(1,1,1)}$ is positioned on the coordinate (0|0), $S_{(1,1,2)}$ on the coordinate (0|b/10) (where b=width of the fields, and width of the fields=width of the screen/n, [provided they are smaller than the height, otherwise the height of the screen]). This is followed by the next line: $S_{(1,2,1)}$=$S_{(1,1,2)}$=(0,b/10). $S_{(1,3,1)}$=$S_{(1,2,2)}$=(0,b*2/10) and $S_{(1,9,1)}=(0, b*9/10)$, $S_{(2,1,2)}=S_{(1,9,2)}$ $(0,b)$. The points of the individual lines are calculated as follows:

$$S_{(i,k,1)}([i-1]*b|[i-1]*b+[k-1]/10*b)$$

$$S_{(i,k,2)}([i-1]*b|[i-1]*b+[k-1]/10*b+b/10)$$

where n=10; i=1 ... n, k=1 ... and b=width of the screen/n

The points (H) are calculated analogously for the horizontal points of the grid lines as follows:

$$H_{(i,k,1)}([i-1]*b+[k-1]/10*b|[i-1]/10*b)$$

$$H_{(i,k,2)}([i-1]*b+[k-1]/10*b+b/10|[i-1]*b)$$

where n=10; i=1 ... n, k=1 ... and b=width of the screen/n

Calculation of the Indices

All points of all lines are checked to determine whether they are still on "their" zero line. If this is not the case, the absolute value of the deviation per point is summed, alternatively the absolute value for the slope can be calculated for each line of and summed to provide the index:

| Point | Target | Actual | Deviation | Slope: $m = \Delta x / \Delta y$ | Location |
|---|---|---|---|---|---|
| $S_{(2, 2, 1)}$ | (b \| b*11/10) | (b \| b*11/10) | 0 | m = (b − b) = 0 | 0 |
| $S_{(2, 2, 2)}$ | (b \| b*12/10) | (b + 1 \| b*12/10) | 1 | | 1/5.65 = 0.18 |
| $S_{(2, 3, 2)}$ | (b*13/10 \| 0) | (b*13/10 \| 0) | 0 | | 0 |
| $H_{(2, 5, 1)}$ | (b*14/10 \| 0) | (b*14/10 \| 1) | 1 | m = 37*b/1 = 37*b | 1/5.02 = 0.2 |
| $H_{(2, 5, 2)}$ | (b*51/10 \| b) | (b*51/10 \| b − 1) | \| −1 \| = 1 | | 1/4 = 0.25 |
| Sum: | | | | | 0.81 |
| 1 + ln(sum) | | | | | 0.79 |

Distance of the Viewer

To ensure that the lines are each spaced one degree apart from each other on any kind of screen, the distance of the viewer (the eye to be examined) is calculated as follows:

$$F_g = b/x_{dpi} \text{ or } F_g = b/y_{dpi}$$

b=width of the screen/n (or screen height, if smaller than the screen width)

$$\text{Distance} = F_g / \tan(1°)$$

where
b=width of the field
n=number of fields
$X_{dpi}$=screen resolution in x-direction=points per inch in x-direction or $y_{dpi}$ if the screen height is smaller than the screen width)

Upon completion of one eye examination, the device may prompt the patient for an examination of the second eye. Patients typically have the option of first completing the metamorphopsia test and then performing the scotoma test, or they can perform both tests in combination.

The user decides which results are to be stored and sends the results, preferably encrypted, to his treating doctor.

Patients can perform the examination at intervals recommended by their doctor or at intervals they choose themselves after noticing symptoms.

Results of the Clinical Trial
Methods:
I. In a pretest that measured sensitivity, specificity, objectivity, reliability and construct validity of the metamorphopsia module of the device according to the invention, 34 patients (68 eyes) were examined who were between 37 to 91 years of age who had the following diagnoses:

13 exudative age-related macular degeneration,
40 normal macules,
1 keratoconus (1) with no maculopathy,
1 macular edema due to central retinal vein thrombosis,
1 macular pucker,
10 drusen of macula (2),
1 diabetic macular edema,
1 central serous maculopathy (2).

II. In a second series, 19 eyes (24 to 91 years of age) with documented maculopathy were examined by Spectral Domain Optical Coherence Tomography (SD-OCT). Examinations were performed using the metamorphopsia module alone, or in combination with the scotoma module, and with the current gold standard, the Amsler test.

The following were investigated.
5 age-related macular degenerations with macular edema,
10 age-related macular degenerations with drusen,
2 macular pucker,
1 macular degeneration due to nearsightedness,
1 central serous retinopathy (RCS).

| N = 19 | Positive AMD index | Negative AMD index |
|---|---|---|
| Without field of vision module | 16 | 3 |
| With field of vision module | 18 | 1* |

By adding the field of vision module, the sensitivity of the test increased: 2 eyes, which were not detected as diseased by the metamorphopsia module alone, were accurately classified as diseased using the combination of the metamorphopsia module and the field of vision module. Due to a large expansion of dry macular degeneration, these two eyes had a large central field of vision loss: For this reason, they did not perceive any distortion, as they were not able to see anything in the central field of vision. One eye* with central serous retinopathy did not show any clinical abnormalities: visual acuity was in the normal range, there were no distortions or visual field losses.

III. In a prospective observational clinical pilot study, the inventors of the present invention examined the monocular best corrected visual acuity (log MAR, BCVA), vision-related quality of life (National Eye Institute Visual Function Questionnaire NEI VFQ 25), slit lamp findings, funduscopic examination on medically dilated pupils, SD-OCT (Spectral Domain Optical Coherence Tomography), Optomap fundus photography, the Amsler grid test and the metamorphopsia module using the device according to the invention, with appropriate near-vision correction on 13 eyes of 13 white patients (6 male, 7 female, 37 to 91 years of age) with macular edema before and after a therapy consisting of three intravitreal injections of anti-vascular endothelial growth factor administered at monthly intervals. The diagnoses for treatment were wet age-related MD=12, myopia associated with MD=1. Concomitant eye diseases were glaucoma in one eye; 1 eye developed a clinically significant cataract during treatment.

All data were collected in accordance with GCP (Good Clinical Practice) and GSP (Good Statistical Practice), as described in the Declaration of Helsinki 1995 and Edinburgh 2000. Prior to the study, after being informed, all patients submitted a statement declaring their consent to participate in the study and to the subsequent processing and publication of the data.

Results

A) Pretests, objectivity, confirmed reliability and construct validity.

In healthy eyes, neither the Amsler test nor the device according to the invention revealed any pathological findings.

The reliability was demonstrated by repeating the test with the device according to the invention a few hours later with the same settings. When screening for maculopathies, the sensitivity of the device according to the invention was 88%, and the specificity was 97%. The $Chi^2$ test resulted in rejection of the null hypothesis ($chi^2$>3.84; degree of freedom=1, alpha=0.05).

B) When a wider range of macular diseases was included, the additional use of the scotoma module of the present device increased the sensitivity of 0.88 to 0.94. One eye with RCS was not recognized by any module. The likelihood of recognizing macular disease without metamorphopsia (e.g., in cases with dry AMD) was improved when both inventive modules were used (OR 3.37; 95% Cl: 0.94-5.67).

C) All parameters were significantly changed after treatment: anti-VEGF improved the SD-OCT findings and the inventive metamorphopsia and scotoma indices that were measured in all 13 eyes using the device according to the invention.

The average decrease in central retinal thickness (CRT) as determined by SD-OCT was 77.54 µm; (median 55 µm; SD 49.99 Cl 111.74; 43.33), the average reduction of the metamorphopsia index was 6.0 (median 4.76; SD 3.5; Cl 7.9; 4.1).

The geometric mean of the BCVA value was 0.38 log MAR (SD 0.28) prior to and 0.25 log MAR (SD 0.21) after treatment (Cl 0.21; 0.03). NEI VFQ 25 increased (QL+) in 11 cases and worsened in 2 patients (QL-) (mean change, 10.69; median 10; SD 12.96; Cl 17.74; 3.65), one of the two patients with reduced quality of life developed a cataract, which led to worsening of visual acuity. A second patient with reduced vision-related quality of life was stable with respect to visual acuity but developed visual field losses due to the appearance of glaucoma.

The measured metamorphopsia index results according to the invention correlated very well with the central retinal thickness measured by SD-OCT, the BCVA value, the Amsler test, and the Visual Function Questionnaire of the National Eye Institute (NEI-VFQ 25).

Patients' vision-related quality of life depends on the location (central disorders cause higher impairment than peripheral disorders), size, and extent of the distortion and field of vision losses. The center of the retina contains the highest density of neurons in the retina. Anatomical changes lead to distortions and visual field losses that are perceived as functionally more bothersome the more centrally located and pronounced they are. This neurophysiological circumstance resulted in the algorithm used to calculate the indexes.

Since distortion in the central field of vision is associated with lower quality of life (is perceived as stronger), a point-deviation occurring there is weighted higher than a point deviation occurring in the peripheral field of vision.

Figure 6:
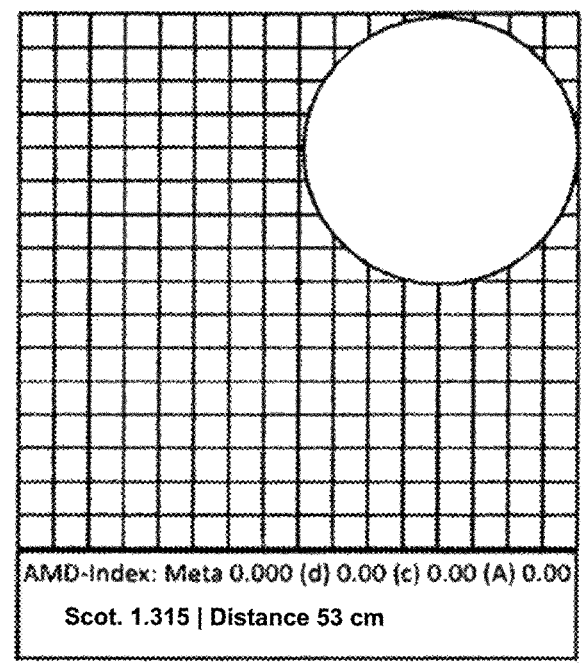
FIG. 6 is a representation of quadrantanopsia obtained by means of the present invention (e.g., with a neurological disease in the optical tract)
Figure 7:
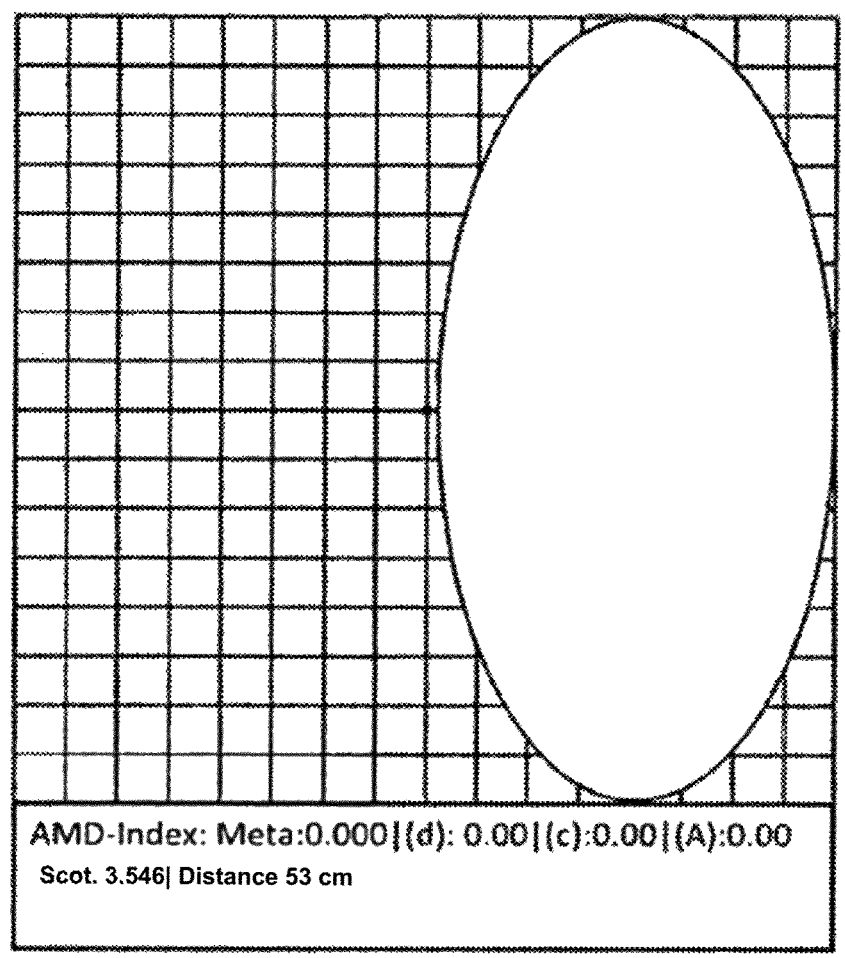
FIG. 7 is representation of a loss in half the visual field (hemianopsia), e.g., after a stroke, obtained by means of the present invention.

FIGS. 6 and 7 show clinical examples where the severity of a field of vision disorder is detected by means of the present invention, where FIG. 6 shows the result of an examination of a patient with quadrant anopsia (e.g., with neurological disease in the optical tract) and FIG. 7 shows the result of an examination of a patient with a unilateral visual field defect (hemianopia), e.g., after a stroke.

In the following, further numbered embodiments of the present invention are disclosed:

1. Method for diagnosing disorders of the field of vision of an eye of a subject, wherein
    a square reticule of a plurality of equidistant parallel horizontal lines and a plurality of equidistant vertical lines and an essentially centrally arranged focus point is displayed on a display device;
    each individual line of the square reticule can be changed into a curve by at least one input signal which is suitable to transform the nonlinear square reticule perceived by the subject as curved due to the disorder in the field of vision into the original square reticule again;
    the boundary lines of each field of the square reticule is defined by boundary functions, which in an initial state are each displayed as lines so that the individual fields are geometrically present as squares and are displayed as such by the display device, but are in part perceived as curved by subjects with disorders in the field of vision; and
    the boundary lines which are perceived as curved can be modified by a series of input signals which modify the boundary curves defined by the boundary functions—and not only the intersection points of the vertical and horizontal lines of the reticule—in such a way that the original linear reticule can be perceived,
    wherein
    the geometric deviations, caused by transformation of the regions of the square reticule perceived as curved, from the originally present squares are determined quantitatively as the sum of the absolute values of the horizontal deviations and as the sum of the absolute values of the vertical deviations.

2. Diagnostic method according to embodiment 1, wherein the boundary functions are selected from the group consisting of: splines, B-splines, non-uniform rational B-splines, cubic splines, Bézier curves, quadratic, cubic, or mixed-rational Bézier curves; Bernstein polynomials; polynomials equal to or greater $2^{nd}$ degree; polygon chains; polygon chains calculated using the De-Casteljau algorithm; other algebraic curves, in particular potency, root, rational and mixed-rational, transcendental functions, in particular exponential, logarithmic, trigonometric, hyperbolic, arcus and area functions.

3. Diagnostic method according to embodiment 1, wherein at least one camera is used to identify the subject and/or to determine in which eye field of vision disorders are to be quantitatively detected.

4. Diagnostic method according to embodiment 1, wherein covering means are used for the eye that is not being tested.
5. Diagnostic method according to embodiment 1, wherein retina and/or iris scans are used to identify the subject and to unambiguously associate the examined eye with the subject.
6. Diagnostic method according to embodiment 1, wherein an eye-tracking system is used for focus control.
7. Diagnostic method according to embodiment 1, wherein an ultrasonic sensor is used to measure the distance between the screen and the user.
8. Diagnostic method according to embodiment 1, wherein geometric deviations caused by transformation are determined independently of the boundary function.
9. Diagnostic method according to embodiment 1, wherein a distortion index/metamorphopsia index and/or a visual field loss index (scotoma index) is calculated from the determined horizontal and vertical deviations.
10. Diagnostic method according to embodiment 1, wherein the distortion index and the scotoma index are weighted as a function of the distance from the focus point, where disorders that are closer to the focus point are weighted more heavily.
11. Diagnostic method according to embodiment 1, wherein the index evaluator (e.g., ophthalmologist, optometrist) can receive and analyze the data via encrypted e-mail, and a warning is automatically sent to the evaluator and/or patient after a threshold value is exceeded.
12. Diagnostic method according to embodiment 1, wherein the change in the size of areas affected by the disorder can be represented by equation (1):

$$\text{Total deviation} = Lg_B(1 + \text{horizontal deviation} + \text{vertical deviation}) \quad (1)$$

where $Lg_B$ is the logarithm base B with B>1, where $Lg_B$ is in particular the natural logarithm,
where an eccentricity is given according to equation (2):

$$\text{Eccentricity} = \sqrt[4]{((x-F_b/2)^2 + (y-F_b/2)^2)} \quad (2),$$

where $F_b$ is the field width (width of the grid), x is a horizontal coordinate and y denotes a vertical coordinate of a point viewed in the grid field;
wherein
a horizontal deviation of a point from the undistorted line is defined according to equation (3) as:

$$\text{Horizontal deviation} = \Delta x/\text{eccentricity}^2 \quad (3),$$

and where a vertical deviation of a point from the undistorted line is defined according to equation (4) as:

$$\text{Vertical deviation} = \Delta y/\text{eccentricity}^2 \quad (4),$$

with $\Delta x$ and $\Delta y$ = deviation from the original value on the undistorted line.
13. Diagnostic method according to embodiment 1, where the device for performing the diagnostic method is a PC, a notebook, a tablet computer, or a smart phone.
14. Diagnostic method according to embodiment 1, where the disorders in the field of vision of an eye is caused by: ocular diseases that lead to macular edema, age-related macular degeneration (AMD), diabetic macular edema, edema following retinal vein thrombosis, macular degeneration caused by myopia, macular edema after cataract surgery and in inflammatory diseases (uveitis, central serous retinopathy).
15. Diagnostic method according to embodiment 1, where a metamorphopsia index ($M_g$) is calculated according to the following rule:

$$Ex = \sqrt{\left(x - \frac{Fb}{2}\right)^2 + \left(y - \frac{Fb}{2}\right)^2} \quad (1)$$

Ex=eccentricity;

$$q_v = |x_{deviation}| \quad (2)$$

$$q_h = |y_{deviation}| \quad (3)$$

$q_v$=deviation in horizontal direction; $q_h$=deviation in vertical direction $x_{deviation}$ in mm; $y_{deviation}$ in mm $$Dx = \sum_{i=1}^{Fb} \frac{50}{Ex^2 + 50} \quad (4)$$

$$Dy = \sum_{i=1}^{Fb} \frac{50}{Ex^2 + 50} \quad (5)$$

$F_b$=field width (width of the grid)
$D_x$=deviation in horizontal direction; $D_y$=deviation in vertical direction $$W_1 = \log\left(\left(\sum_{i=1}^{Fb} q_i\right) + 1\right) \quad (6)$$

$W_1$=distortion amplitude $$W_2 = \log\left(\left(\sum_{i=1}^{Fb} \frac{50}{Ex_i^2 + 50}\right) + 1\right) \quad (7)$$

$W_2$=distortion eccentricity $$W_3 = \log\left(\left(\frac{\sum_{i=1}^{Fb*4} VP_i}{(\sum n)^2} * 100\right) + 1\right) \quad (8)$$

$W_3$=distortion area
VPi=moved Bézier control points
n=number of fields displayed, resp. number of vertical or horizontal lines $$M_g = (\log(D_x + D_y + 1) + W_3) * 1.3 \quad (9)$$

LITERATURE

1. Klatt, C., et al., [*Diagnostics of metamorphopsia in retinal diseases of different origins*]. Ophthalmologe, 2006, 103 (11): p. 945-52.
2. Roche. *Lamalizumab*. 2015.
3. DOB, B., ROG. *Leitlinie Nr. 21: Altersabhängige Makuladegeneration*. 2011.

4. Finger R P, F. R., Holz F G et al, *Incidence of blindness and severe visual impairment in Germany: projections for 2030.* Invest Ophthalmol. Vis. Sci, 2011. 52: p. 4381-9.
5. Bertram, B., *Blindheit and Sehbehinderung in Deutschland: Ursachen und Häufigkeit.* Der Augenarzt, 2005, 39.
6. DOG. B., ROG, *Leitlinie Nr. 21: Altersabhängige Makuladegeneration.* 2011.
7. DOG, B., ROG, *Die Anti-VEGF—Therapie bei der neovaskulären altersabhängigen Makuladegeneration: Therapeutische Strategien* 2014.
8. Rosenfeld P J, M. A., Tennant M T S. *Opthalmology: Age related macular degeneration.* Opthalmology. 3rd edn. Yanoff M, Duker J S. Philadelphia: Mosby/Elsevier; 2009: 2009: p. 658.673.
9. Deloitte.
10. Amsler, M., *Die Untersuchung des qualitativen Sehens mit dem quadratischen Netz. Anweisung zum Gebrauch der Testtafeln.* Theodore Hamblin LTD. 1958.
11. Claessens, D., *Gegenüberstellung von sihkraftbezogener Lebensqualität and Visusverlauf nach intravitrealer Anti-VEGF Therapie bei altersbedingter feuchter Makuladegeneration* 2010.
12. Finger. R. P., et al., *Quality of life in age-related macular degeneration: a review of available vision-specific psychometric tools.* Qual Life Res, 2008. 17(4): p. 559-74.
13. Hotz, F. G., et al., *Multi-country real-life experience of anti-vascular endothelial growth factor therapy for wet age-related macular degeneration.* Br J Ophthalmol. 2014.
14. Wolf. A. and A. Kampik. *Efficacy of treatment with ranibizumab in patients with wet age-related macular degeneration in routine clinical care: data from the COMPASS health services research.* Graefes Arch Clin Exp Ophthalmol. 2014. 25244): p. 647-55.
15. Finger, R. P., et al., *Treatment patterns, visual acuity and quality-of-life outcomes of the WAVE study—a noninterventional study of ranibizumab treatment for neovascular age-related macular degeneration in Germany.* Acta Ophthalmol, 2013. 91(6): p. 540-6.
16. Zeiss, SD-OCT. 2015.
17. Mangione, C. M., et al. *Development of the 25-item National Eye Institute Visual Function Questionnaire.* Arch Ophthalmol, 2001. 119(7): p. 1050-8.
18. ORCA Heymes. B.: Evaluierung der SD-OCT Befundung in der täglichen Praxisroutine (B)
19. CATT Martin, D. F.: Comparison of AMD Treatment Trial

The invention claimed is:

1. A device for the quantitative detection and/or monitoring of disorders in the field of vision of an eye of a subject comprising:

a display device;

at least one control device for the display device and at least one processor and at least one storage device, wherein the device projects to the display device a square reticule consisting of a plurality of parallel equidistant horizontal lines and a plurality of equidistant parallel vertical lines with defined spacing and an essentially centrally arranged focus point, wherein each individual line of the square reticule can be changed into a curve by at least one input signal which is suitable to transform the nonlinear square reticule perceived by the subject as curved due to the disorder in the field of vision into the original square reticule again, wherein the boundary lines of each field of the square reticule is defined by boundary functions, which in an initial state are each displayed as lines so that the individual fields are geometrically present as squares and are displayed as such by the display device, but are in part perceived as curved by subjects with disorders in the field of vision; and the boundary lines which are perceived as curved can be modified by a series of input signals which modify the boundary curves defined by the boundary functions—and not only the intersection points of the vertical and horizontal lines in the reticule—in such a way that the original linear reticule can be perceived, wherein the geometric deviations caused by transformation of the regions of the square reticule perceived as curved from the originally present squares are determined quantitatively as the sum of the horizontal deviations and as the sum of the absolute values of the vertical deviations, wherein the boundary functions are selected from the group consisting of: splines, B-splines, non-uniform rational B-splines, cubic splines, Bézier curves, quadratic, cubic or mixed-rational Bézier curves; Bernstein polynomials; polynomials equal to or greater $2^{nd}$ degree; polygon chains; polygon chains calculated using the De-Casteljau algorithm; other algebraic curves, in particular potency, root, rational and mixed-rational, transcendental functions, in particular exponential, logarithmic, trigonometric, hyperbolic, arcus and area functions.

2. The device of claim 1, wherein the device is a PC, a notebook, a tablet computer, or a smart phone.

3. The device of claim 1, wherein at least one camera is provided on the device.

4. The device of claim 1, wherein covering means are provided for the eye that is not being examined.

5. The device of claim 1, wherein retina and/or iris scans are used to identify the subject and to unambiguously associate the examined eye or the focus on the central point with the subject.

6. The device of claim 1, wherein said device is designed as eyeglasses, in particular a diving mask, where display devices are provided instead of eyeglass lenses.

7. The device of claim 1, wherein the geometric deviations caused by transformation are determined independently of the boundary function.

8. The device of claim 1, wherein a distortion index (metamorphopsia index) and/or a visual field loss index (scotoma index) is calculated from the determined horizontal and vertical deviations.

9. The device of claim 8, wherein the distortion index and the visual field loss index are weighted as a function of the distance from the focus point, where disorders that are closer to the focus point are weighted more heavily.

10. The device of claim 1, wherein the change in the size of areas affected by the disorder can be represented by equation (1):

$$\text{Total deviation} = Lg_B(1 + \text{horizontal deviation} + \text{vertical deviation}) \qquad (1)$$

where $Lg_B$ is the logarithm base B with B>1, where $Lg_B$ is in particular the natural logarithm, where an eccentricity is given according to equation (2):

$$\text{Eccentricity} = \sqrt{((x - F_b/2)^2 + (y - F_b/2)^2)}, \qquad (2),$$

where $F_b$ is the field width (width of the grid), x is a horizontal coordinate and y denotes a vertical coordinate of a point viewed in the grid field;
wherein
a horizontal deviation of a point from the undistorted line is defined according to equation (3) as:

Horizontal deviation=$\Delta x$/eccentricity$^2$ (3), and where a vertical deviation of a point from the undistorted line is defined according to equation (4) as:

Vertical deviation=$\Delta y$/eccentricity$^2$ (4), where $\Delta \chi$ and $\Delta y$=deviation from the original value on the undistorted line.

11. The device of claim 1, wherein the metamorphopsia index ($M_g$) is calculated according to the following rule:

$$Ex = \sqrt{\left(x - \frac{Fb}{2}\right)^2 + \left(y - \frac{Fb}{2}\right)^2} \qquad (1)$$

Ex=eccentricity;

$$q_v = |x_{deviation}| \qquad (2)$$

$$q_h = |y_{deviation}| \qquad (3)$$

$q_v$=deviation in horizontal direction; $q_h$=deviation in vertical direction $x_{deviation}$ in mm; $y_{deviation}$ in mm $$Dx = \sum_{i=1}^{Fb} \frac{50}{Ex^2 + 50} \qquad (4)$$

$$Dy = \sum_{i=1}^{Fb} \frac{50}{Ex^2 + 50} \qquad (5)$$

$F_b$=field width (width of the grid)
$D_x$=deviation in horizontal direction; $D_y$=deviation in vertical direction $$W_1 = \log\left(\left(\sum_{i=1}^{Fb} q_i\right) + 1\right) \qquad (6)$$

$W_1$=distortion amplitude $$W_2 = \log\left(\left(\sum_{i=1}^{Fb} \frac{50}{Ex_i^2 + 50}\right) + 1\right) \qquad (7)$$

$W_2$=distortion eccentricity $$W_3 = \log\left(\left(\frac{\sum_{i=1}^{Fb*4} VP_i}{(\sum n)^2}\right)*100\right) + 1\right) \qquad (8)$$

$W_3$=distortion area
VPi=moved Bézier control points
n=number of fields shown, resp. number of vertical or horizontal lines $$M_g = (\log(D_x + D_y + 1) + W_3)*1.3. \qquad (9)$$

12. The device of claim 1 wherein the metamorphopsia index $M_g$ is in the range between 0.01 and 4, where the value is <0.5 in people with healthy retinas and between 0.6 and 4 in the presence of macular disease.

13. The device of claim 1, wherein the scotoma index ($S_g$) is calculated according to the following rule:

$$S_A = \frac{S_x * S_y * \pi * 30}{Fb^2} \qquad (1)$$

where $S_x$=length of the x-axis and
$S_y$=length of the y-axis and
Fb=field width of the grid $$S_E = \frac{Fb}{2 * \sqrt{\left(Es_x - \frac{Fb}{2}\right)^2 + \left(Es_y - \frac{Fb}{2}\right)^2}} \qquad (2)$$

where Fb=field width of the total grid and
$E_{Sx}$=x—component of eccentricity of the centroid of the ellipse and
$E_{Sy}$=y—component of eccentricity of the centroid of the ellipse $S_g = \log(S_A * S_E + 1)$.

14. A method for quantitative measurement of disorders in the field of vision of an eye of a subject, wherein
a square reticule of a plurality of equidistant parallel horizontal lines and a plurality of equidistant vertical lines and an essentially centrally arranged focus point is displayed on a display device;
each individual line of the square reticule can be changed into a curve by at least one input signal which is suitable to transform the nonlinear square reticule perceived by a subject as curved into the original square reticule again;
the boundary lines of each field of the square reticule is defined by boundary functions, which in an initial state are each displayed as lines so that the individual fields are geometrically present as squares and are displayed as such by the display device, but are in part perceived as curved by subjects with disorders in the field of vision; and
the boundary lines perceived as curved can be modified by a series of input signals which modify the boundary curves defined by the boundary functions—and not only the intersection points of the vertical and horizontal lines in the reticule—in such a way that the original linear reticule can be perceived,
wherein
the geometric deviations caused by transformation of the regions of the square reticule perceived as curved, from the originally present squares are quantitatively determined as the sum of the absolute values of the horizontal deviations and as the sum of the absolute values of the vertical deviations,
wherein the boundary functions are selected from the group consisting of: splines, B-splines, non-uniform rational B-splines, cubic splines, Bézier curves, quadratic, cubic or mixed-rational Bézier curves; Bernstein polynomials; polynomials equal to or greater $2^{nd}$ degree; polygon chains; polygon chains calculated using the De-Casteljau algorithm; other algebraic curves, in particular potency, root, rational and mixed-rational, transcendental functions, in particular exponential, logarithmic, trigonometric, hyperbolic, arcus and area functions.

15. The method of claim 14, wherein at least one camera is used to identify the subject and/or to determine in which eye disorders in the field of vision are to be quantitatively detected.

16. The method of claim 14, wherein covering means are used for the eye that is not being tested.

17. The method of claim 14, wherein retina and/or iris scans are used to identify the subject and to unambiguously associate the examined eye with the subject and his focus control.

18. The method of claim 14, wherein an ultrasonic sensor is used to measure the distance between the screen and the subject in order to clearly present the line spacing in degrees° on the display device.

19. The method of claim 14, wherein geometric deviations caused by transformation are determined independently of the boundary function.

20. The method of claim 14, wherein a distortion index/metamorphopsia index and/or a visual field loss index (scotoma index) is calculated from the horizontal and vertical deviations determined.

21. The method of claim 20, wherein the distortion index and the scotoma index are weighted as a function of the distance from the focus point, where disorders that are closer to the focus point are weighted more heavily.

22. The method of claim 14, wherein the change in the size of areas affected by the disorder can be represented by equation (1):

$$\text{Total deviation} = Lg_B(1 + \text{horizontal deviation} + \text{vertical deviation}) \tag{1}$$

where $Lg_B$ is the logarithm base B with B>1, where $Lg_B$ is in particular the natural logarithm, where an eccentricity is given according to equation (2):

$$\text{Eccentricity} = \sqrt{((x - F_b/2)^2 + (y - F_b/2)^2)} \tag{2},$$

where $F_b$ is the field width (width of the grid), x is a horizontal coordinate and y denotes a vertical coordinate of a point viewed in the grid field; wherein a horizontal deviation of a point from the undistorted line is defined according to equation (3) as:

$$\text{Horizontal deviation} = \Delta x / \text{eccentricity}^2 \tag{3},$$

and where a vertical deviation of a point from the undistorted line is defined according to equation (4) as:

$$\text{Vertical deviation} = \Delta y / \text{eccentricity}^2 \tag{4},$$

where $\Delta \chi$ and $\Delta y$=deviation from the original value on the undistorted line.

23. The method of claim 14, wherein a PC, a notebook, a tablet computer or a smart phone is used as device for performing the method.

* * * * *

UNITED STATES PATENT AND TRADEMARK OFFICE
CERTIFICATE OF CORRECTION

PATENT NO. : 10,588,506 B2
APPLICATION NO. : 15/752735
DATED : March 17, 2020
INVENTOR(S) : Claessens et al.

It is certified that error appears in the above-identified patent and that said Letters Patent is hereby corrected as shown below:

In the Specification

Column 5, Line 65: "metamorphopsia" should read "metamorphosias";

Column 6, Line 24: "Abstract" should read "abstract";

Column 10, Line 43: "Macula" should read "macula";

Column 10, Line 63: "v" should read "√";

Column 11, Line 5: "delta chi" should read "delta x";

Column 11, Line 11: "delta chi" should read "delta x";

Column 12, Line 41: "Studies" should read "studies";

Column 12, Line 42: "that patients were neglected in clinical practice when diagnostic procedures were used" should be replaced with "less diagnostic procedures than desirable";

Column 13, Line 15: delete "HIV infection";

Column 14, Line 23: "sheet separation" should read "epithelial detachment";

Column 14, Line 44: "decides" should read "decide";

Column 16, Line 47: "peripherally" should read "peripheral";

Column 16, Line 62: insert --is-- before "considerably";

Signed and Sealed this
First Day of September, 2020

Andrei Iancu
*Director of the United States Patent and Trademark Office*

CERTIFICATE OF CORRECTION (continued)
U.S. Pat. No. 10,588,506 B2

Column 17, Line 58: "The index growing with increasing quality of life of the test for detecting the subjectively experienced quality of like NEI VFQ-25" should be replaced with "The subjectively experienced vision related quality of life measured as NEI VFQ-25 score";

Column 18, Line 66: "Sg" should read "g";

Column 20, Line 14: the first occurrence of "Length" should read "length";

Column 20, Line 52: "Advanced macular edema" should read "intermediate or late AMD";

Column 20, Line 65: "Advanced macular edema" should read "intermediate or late AMD";

Column 21, Line 67: the formula should read "H(i,2)([i-1] * b + b/2 | [i-1] * b)";

Column 23, Line 1: "= =" should read "=";

Column 24, Line 2: "macules" should read "macula";

Column 24, Line 21: "RCS" should read "CSR";

Column 24, Line 50: delete the "*";

Column 24, Line 50: insert a -- - -- before "25";

Column 25, Line 1: "MD" should "macular degeneration";

Column 25, Line 2: "MD" should "macular degeneration";

Column 25, Line 31: "RCS" should read "CSR";

Column 25, Line 55: delete "the appearance of";

Column 26, Line 5: "stronger" should be replaced with "more bothersome"; and

Column 27, Line 57: "delta chi" should read "delta x".